United States Patent [19]
Humphreys

[11] Patent Number: 5,679,527
[45] Date of Patent: Oct. 21, 1997

[54] MODIFICATION OF POLYPEPTIDE STRUCTURE

[75] Inventor: Robert E. Humphreys, Acton, Mass.

[73] Assignee: Antigen Express, Inc., Worcester, Mass.

[21] Appl. No.: 291,601

[22] Filed: Aug. 15, 1994

Related U.S. Application Data

[63] Continuation-in-part of Ser. No. 857,327, Mar. 25, 1992, abandoned, and Ser. No. 63,908, May 19, 1993, abandoned.

[51] Int. Cl.$^6$ .................................................. G01N 33/53
[52] U.S. Cl. .................. 435/7.1; 436/501; 364/413.01; 364/496; 364/497; 364/499
[58] Field of Search ................ 435/7.1, 7.2; 436/501; 424/184.1, 185.1; 364/413.01, 496, 497, 499

[56] References Cited

PUBLICATIONS

Lu et al Tibtech, vol. 9, Jul. 1991 pp. 238–242 "Common Principles in Protein Folding and Antigen Protection".
Reyes et al., *J. Biol. Chem.* 264: 12854 (1989).
Reyes et al., *Mol. Immunol.* 27: 1021 (1990).
Stille et al., *Mol. Immunol.* 24: 1021 (1987).
Rennell et al., *J. Biol. Chem.* 267: 17748 (1992).
Reyes et al., *Mol. Immunol.* 25:867 (1988).
Torgerson et al., *J. Biol. Chem.* 266: 5521 (1991).
Lu et al., *J. Immunol.* 145: 899 (1990).
Lu et al., *J. Biol. Chem.* 266: 10054 (1991).
Vazquez, et al., *J. Biol. Chem.* 267: 1 (1992).

*Primary Examiner*—Lora M. Green
*Attorney, Agent, or Firm*—Kevin M. Farrell

[57] ABSTRACT

Disclosed in the present application are methods for the identification of favored and suppressed patterns of hydrophobic and nonhydrophobic amino acids in naturally occurring proteins and polypeptides. Methods are disclosed which enable protein structure alteration based on information gained from hydrophobicity pattern analysis.

1 Claim, 1 Drawing Sheet

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

Leu Tyr Gln Glu Leu Gln Lys Leu Thr Gln Thr Leu Lys
    1                 5                        10

( 2 ) INFORMATION FOR SEQ ID NO:2:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

Leu Tyr Gln Glu Leu Gln Lys Leu Leu Gln Thr Leu Lys
    1                 5                        10

( 2 ) INFORMATION FOR SEQ ID NO:3:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

Leu Tyr Gln Glu Leu Gln Lys Leu Thr Leu Thr Leu Lys
    1                 5                        10

MODIFICATION OF POLYPEPTIDE STRUCTURE

RELATED APPLICATIONS

The present application is a continuation-in-part of U.S. application Ser. No. 07/857,327, filed Mar. 25, 1992, now abandoned, and U.S. application Ser. No. 08/063,908, filed May 19, 1993, now abandoned, the disclosures of which are incorporated herein by reference.

BACKGROUND OF THE INVENTION

The initial phase of the folding of amino acid copolymers (peptides, polypeptides, and proteins) is hypothesized to be based on the coalescence of hydrophobic side chains of the copolymer either within its core or against a hydrophobic surface. The mechanisms by which these events occur have not been well defined. The ability to identify, with precision, the roles of the hydrophobic residues placed in nonhydrophobic positions of motifs defined by the hydrophobic residues would lead to new avenues of applied research.

SUMMARY OF THE INVENTION

The subject invention relates to two complementary methods for establishing favored and suppressed patterns of hydrophobic residues from the group leucine, isoleucine, valine, phenylalanine, and methionine in (a) alpha helices of proteins and (b) throughout proteins without restriction to their alpha helices.

The first of the complementary methods requires the establishment of template-specified positions of amino acids in a primary sequence with respect to application of a longitudinal, hydrophobic strip-of-helix template to a known or putative helix within an amino acid sequence. The method comprises providing an amino acid sequence comprising a known or putative helix and applying the longitudinal strip-of-helix template:

to the amino acid sequence of the known or putative helix to maximize the mean hydrophobicity of residues in ☐ positions. The template pattern is then extended to adjacent non-helical regions. The template-specified positions enable predictions which can be used to alter the structure, and thereby function, of an amino acid copolymer. For example, such predictions can be used to alter helical length.

The template specified above can also be employed in connection with a method for predicting helices in an amino acid copolymer. The method comprises providing an amino acid sequence to be analyzed for the presence of a helix. The predictor algorithms ○○○☐○○○☐○○☐○○ and ○○○☐○○☐○○○☐○○ are applied to the sequence with a positive selection requiring the mean hydrophobicity of ☐ positions being greater than or equal to 3.0 on the Kyte-Doolittle scale of hydrophobicity.

Overlapping positive selections are merged. The longitudinal strip-of-helix template ☐●▲●☐○○☐●▲●☐○○☐●▲○ is then applied to the merged overlapping positive selections to maximize the mean hydrophobicity of residues in ☐ positions. The confidence of a prediction is then ranked based on the identification of a concordance of observed residues with the idealized residue-position assignments.

The second complementary method for establishing favored and suppressed patterns of hydrophobic residues from the group Leu, Ile, Val, Phe, and Met (indicated ♦) and other residues (indicated ◊) is applicable throughout the primary sequence of an amino acid copolymer without restriction to alpha helices. This method requires initial analysis of a statistically significant number of naturally occurring proteins. Statistically significant, as used in this context, means a number sufficient to reveal the pattern disclosed in Example 11 (48 proteins were analyzed in Example 11). Templates of from 3 to 9 positions composed of all combinations of ♦ and ◊ in each position are applied to the amino acid sequences of the naturally occurring proteins. The frequency with which each template is found is scored and the standard deviation by which a template occurs is determined from the expected frequency from an empirical distribution of ♦ and ◊ positions based upon the natural frequencies of the amino acids in the naturally occurring proteins. The patterns are then ranked on a scale of preferred and suppressed on the basis of those standard deviations between observed and expected frequencies. Preferred patterns of hydrophobicity determined in this manner correlate with increased stability as determined, for example, by NMR chemical shift determinations.

DETAILED DESCRIPTION OF THE INVENTION

Figure 1A:
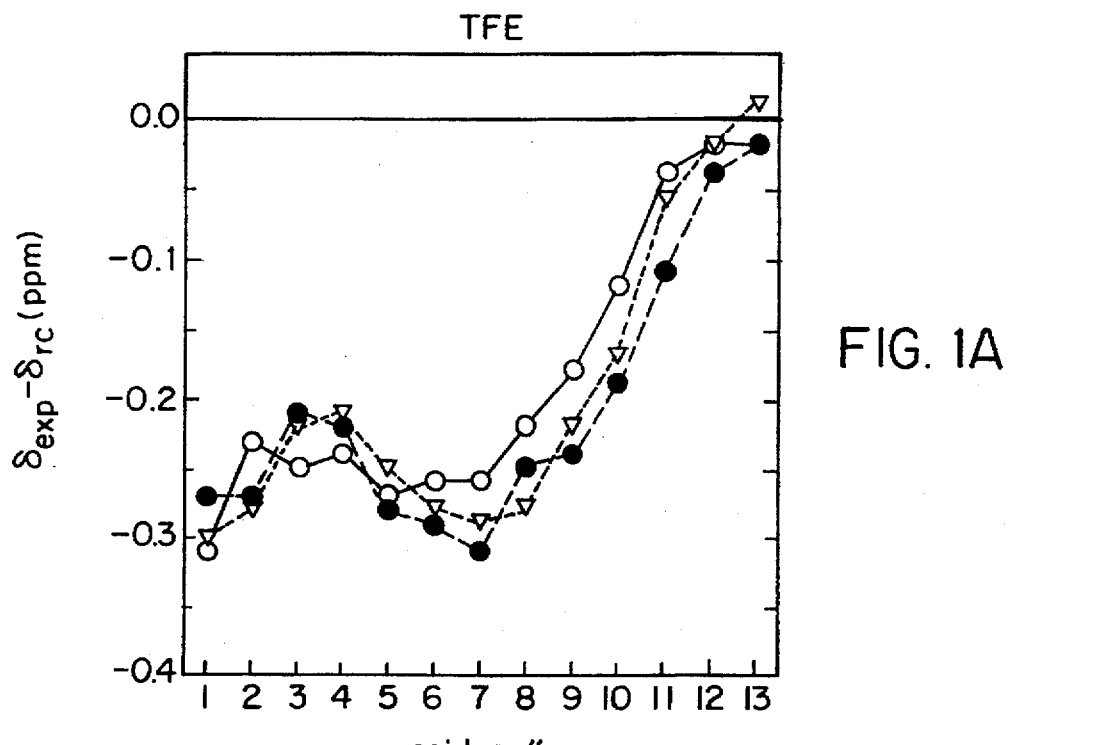
FIGS. 1(A) and 1(B) are diagrams representing the difference between experimentally observed (exp) and random coil (rc) values of the chemical shifts for the C$\alpha$H at each residue position in three peptides.

The subject invention relates to two complementary methods for establishing favored and suppressed patterns of hydrophobic residues from the group leucine, isoleucine, valine, phenylalanine, and methionine. The first of the two complementary methods is based on the finding that the placement of hydrophobic residues (leucine, isoleucine, valine, phenylalanine and methionine) at positions n, n+4, n+7 and n+11 in the primary amino acid sequence of a protein will induce folding as a helix with a longitudinal hydrophobic strip, in almost all naturally occurring helices which were studied. Although not wishing to be bound by theory, this observation can be extended. It is reasonable to postulate, for example, that the anchoring of recurrent hydrophobic side chains along one side of a helix against a hydrophobic surface governs helical folding and adsorption. Examples of a hydrophobic surface can include, the hydrophobic core of a protein, the binding site of a hormone receptor, or a membrane.

This observation led to the development of a method to identify categorical positions in helices based upon a template for the positions of residues on the surface of the cylinder of an alpha helix. Unique distributions of residues in those template defined positions demonstrate the role of some residues in determining the folding, stability and adsorption of helices against hydrophobic surfaces.

The categorical positions in the helix are determined by applying the longitudinal, hydrophobic strip-of-helix template:

to an amino acid copolymer containing a known or putative helix. Conventional methods can be used to predict the presence of a helix, as can other methods disclosed herein. This is best accomplished using computer software which applies the first residue in the circular (infinite) template to the first residue in the helix and sums the mean hydrophobicity of residues in □ positions of that first application of the template. The mean hydrophobicity of residues in □ positions is called the strip-of-helix hydrophobicity index. The hydrophobicity of residues are given in the Kyte-Doolittle or another scale. The computer then applies the second residue in the template to the first residue in the helix in a like manner summing the mean hydrophobicity of residues in the □ positions. Such applications continued with each position in the template being applied to the first residue in the helix. The application with the highest strip-of-helix hydrophobicity index is the "best fit" of the template and that positioning is taken in all analyses which follow. It should be noted that the methods of this invention can be loosely applied to copolymers of small to moderate length without the need for a computer.

There are four categories of positions in the template for the hydrophobic strip-of-helix. Those positions can be displayed in a linear projection of the template or in a sheet projection. These two alternate presentation formats are used conventionally. In the sheet projection, the positions in the primary sequence coil on the cylindrical surface of the helix, as does a stripe on a barber's pole, and can be segregated into longitudinal quadrants. Quadrant III arbitrarily holds the □ positions of the hydrophobic strip-of-helix and quadrants II and IV contain ○ and ●, respectively. The ● positions are close to and the ○ positions are farther away from the longitudinal axis of quadrant III. Quadrant I contains Δ positions occurring in every other cycle around the helix. Once the best fit of the hydrophobic strip-of-helix is determined with residues in the helix, the pattern of the helix can be extended to residues which fall beyond the helical boundaries to define □ and non □ residues beyond the helix.

As discussed in greater detail in the Examples, the distribution of residues in template-predicted positions correlated surprising well with the actual pattern of residue distributions observed in known helices. The preferred distribution of amino acids predicted based upon template-specified positions is the following:

a) leucine, isoleucine, valine, phenylalanine, or methionine in all □ positions in the helix;

b) leucine, isoleucine, valine, phenylalanine, or methionine in the N-terminal □ position in the helix;

c) leucine, isoleucine, valine, phenylalanine, or methionine in the C-terminal □ position in the helix;

d) alanine or valine in the □ position in the helix with the smallest residue e) non(leucine, isoleucine, valine, phenylalanine, or methionine) in the first □ position beyond the helix at the N-terminus;

f) non(leucine, isoleucine, valine, phenylalanine, or methionine) in the first □ position beyond the helix at the C-terminus;

g) non(leucine, isoleucine, valine, phenylalanine, or methionine) in all non□ positions in the helix;

h) aspartate or glutamate or asparagine in the N-terminal non □ positions before the N-terminal □ position; and i) lysine, arginine or histidine in the C-terminal ○ positions after the C-terminal □, or in the first C-terminal □ position after the helix.

The favored residues found in the template-predicted □ positions are the hydrophobic residues leucine, isoleucine, valine, phenylalanine and methionine. The distribution of these residues outside the helical region were found to correlate with levels expected for random distribution. The favored residues found in the non □ positions are non-hydrophobic residues. The presence of hydrophobic residues in the non □ positions would tend to promote the adsorption and folding of the protein or polypeptide to a hydrophobic surface in a manner which does not promote helical formation. For example, a peptide with alternating hydrophobic residues would adsorb as a beta-pleated sheet. Deviation from the template-predicted residues tends to disfavor helix formation. Negatively charged amino acids aspartate and glutamate were found more often in the non□ positions before the N-terminal □ position in helices. Positively charged residues were found more often in non□ positions after the C-terminal □ position in helices and in the first □ position beyond the C-terminus of the helix. Those residues served to stabilize the delta-positive charge at the N-terminus and the delta-negative charge at the C-terminus formed by the helix macrodipole, which is the sum of all the dipoles formed by the hydrogen bonds between amido protons and carbonyl oxygens along the peptidyl backbone. Asparagine was found more often in the non□ positions before the N-terminal □ of the helix. The side chain of asparagine hydrogen-bonded across the diameter of the helix to a peptidyl backbone group on the other side of the helix, thereby stabilizing its N-terminus.

Furthermore, by analyzing the data generated in such experiments, it has become possible to discern special rules which apply to particular template-specified positions. These positions include, for example:

a) the N-terminal □ position;

b) the C-terminal □ position;

c) the □ position in the helix with the smallest residue;

d) the □ position residue in the helix with the least hydrophobic residue;

e) non□ positions in the helix prior to the N-terminal ○ position in the helix; and f) non□ positions in the helix after the C-terminal ○ position in the helix.

In addition, it has been possible to identify template-specified residues which fall outside the helix to which special rules apply. These include:

g) the first □ position beyond the helix at the N-terminus;

h) the first □ position beyond the helix at the C-terminus.

As was discussed above, a strong correlation exists between template-predicted □ positions and hydrophobic residues. This correlation is particularly striking for the N- and C-terminal □ positions which define the extent of the helix. In addition, the presence of a hydrophobic residue in a terminal □ of the helix and the absence of a member of that group from the template-predicted □ falling outside the helix dictates helix termination. The alteration of this pattern leads to extension or shortening of the helix.

It was found that helices tend to cross through their strips and most frequently at least one of the crossing residues was an alanine or valine residue. These are the smallest of the hydrophobic residues. This correlation suggests that crossing of strips through such a residue is a favored, stabile configuration.

From the patterns which have emerged as a result of this analysis predictions with respect to the functional effect of structural alterations can be made with a high degree of certainty. Such structural changes can be exploited in the rational engineering of amino acid copolymers such as proteins and polypeptides.

For example, the structure of an amino acid copolymer can be altered by first applying the strip-of-helix template to a known or putative helix and determining the best fit as previously described. The concordance between template-predicted residues to the residues which actually appear in the copolymer is determined. A structural change is effected by altering the identity of the actual residues.

The alteration can change the identity of a residue to bring the strip into a greater degree of conformance with the template-predicted chemical nature of the residue, or the alteration can create a greater divergence. The former change tends to favor helix formation, whereas the latter tends to disfavor helix formation.

Similar principles can also be used to alter the length of a helical region. The strip-of-helix template is applied to a known or putative helix and the best fit is established. The actual amino acid sequence at the N- and C-terminal □ position and the first □ beyond the termini of the helix is compared with the template-predictions. Helix length is altered by changing the identity of one or more of these residues in accordance with the principles previously discussed. The helix is lengthened by increasing the match between the actual amino acid residues at the identified positions and the template-predicted chemical identity at the positions. The helix is shortened by increasing divergence at these positions.

The unique distributions of amino acids in and near known helices enables the prediction of helices based upon the finding of such distributions. A first method is based upon scoring for two templates ○○○□○○○□○○□○○ and ○○○□○○□○○○□○○ such that the mean hydrophobicity of residues in □ positions is greater than or equal to 3.0 on the Kyte-Doolittle scale. Those individual and merged predictions constitute the endpoint for the first method of predicting helices. It has a high sensitivity (correct predictions/number of true predictions) and efficiency (correct predictions/total number of predictions made).

A second method is based upon the outcome of the first and offers a higher degree of efficiency at the price of moderately lower sensitivity because it is based also on scoring for additional stabilizing residues in template-defined positions. In that method, the merged, predicted helices of method 1, are fitted with a template □●△●□○○□●△●□○○□○△○ and the template positions are scored for the presence of idealized residue-position assignments.

The first of two complementary methods for establishing favored and suppressed patterns of hydrophobic residues from the group leucine, isoleucine, valine, phenylalanine, and methionine, and subsidiary methods based on template specified positions, is discussed above. The second of the two complementary methods for establishing favored and suppressed patterns of hydrophobic residues from the group leucine, isoleucine, valine, phenylalanine, and methionine is based on the discovery of rules which govern the ordering of amino acid residues throughout proteins in general with no restriction to the alpha helices. More specifically, it has been discovered that certain patterns of hydrophobic amino acid residue ordering are favored while other patterns are suppressed by natural selection. Disclosed herein are novel methods to design amino acid copolymers de novo or to modify natural products according to patterns of hydrophobic and nonhydrophobic amino acids both in the primary sequence and in 3-dimensional arrangements within the amino acid copolymer. These methods lead to the most efficiently folded and stable forms of such amino acid copolymers.

Patterns of hydrophobic residues which are naturally favored or suppressed are determined by the analysis of patterns of such residues in a statistically significant number of naturally occurring proteins. More specifically, favored and suppressed patterns of hydrophobic and nonhydrophobic residues in primary amino acid sequences are found by assigning the hydrophobic amino acids Leu, Ile, Val, Phe, and Met (LIVFM) to the group ◆ and all other amino acids to the group ◇. The frequencies of patterns containing all combinations of ◆ and ◇ from 3 to 12 positions are determined in a statistically significant number of more natural proteins (e.g., 30 or more). The patterns are ranked according to the magnitude of their deviations from empirical distributions of the amino acids $|z| \geq 1.96$ ($p \leq 0.05$). For example ◇◆◆◇◇ is favored ($z=3.5$; $p<0.001$), while ◇◆◇◆◇ is suppressed ($z=-3.4$; $p<0.001$). In longer, composite patterns, ◆◆ followed by ◇◇ and one ◆ is favored (◇◇◆◆◇◇◆◇◇, $z=5.1$), while conversion of the single hydrophobic residue to a pair is not (◇◇◆◆◇◇◆◆◇, $z=0.8$). Additional distributions of certain nonhydrophobic amino acids around ◇ positions in strongly favored patterns are also favored or suppressed (Asp, Glu, Lys, Arg, Asn, Cys, Tyr, and Pro; for each $|z|>2.0$).

The natural rules governing the ordering of hydrophobic residues can be applied to the modification of a protein or peptide in a rational drug design scheme. In the design of an amino acid copolymer, the arrangements of hydrophobic and nonhydrophobic residues should include segments with such favored patterns of LIVFM versus nonLIVFM residues occurring at $z \geq 1.96$ ($p \leq 0.05$). Likewise the design should avoid segments with suppressed patterns of LIVFM versus nonLIVFM residues occurring at $z \leq -1.96$ ($p \leq 0.05$). Furthermore, the placements of nonLIVFM residues should parallel the favored and suppressed composite patterns of overlapping or adjacent patterns which are identified with this method. That is, when ◇◆◆◇◇ occurs it should be followed by ◆◇ rather than ◆◆◇ and preceded by ◇◆ rather than by ◇◆◆ or ◇◆◆◇, according to the composite patterns demonstrated in this invention. Suppressed patterns may be employed in design of amino acid copolymers under conditions where ambiguity or flexibility of a segment of an amino acid copolymer is desired.

It is possible that the two complementary methods described above can specify conflicting amino acid identifies under specific circumstances. In the case where modifications in amino acids within one segment of an amino acid copolymer are indicated by both the strip-of-helix hydrophobicity method (based on application of the template □●△●□○○□●△●□○○□●△○) and the method derived from analysis of patterns for Leu, Ile, Val, Phe and Met residues (indicated ◆) and other residues (indicated ◇), specifications by the latter method should be applied to residues following in ○ or ● positions which are identified with the strip-of-helix template method.

The methods of the present invention are useful for the identification and modification of structure of amino acid copolymers which are of natural origin or designed/selected de novo for catalytic or therapeutic purposes. "Modification of structure", as used herein, specifically includes modifications which increase, or decrease, amphiphilic helical structure. Increases in amphiphilic helical structure correlate with increases in stability of the amino acid copolymer. The term "amino acid copolymer", as used herein, is intended to encompass peptides and polypeptides (amino acid copolymers ranging from about 8 to about 100 amino acid residues), as well as proteins.

Peptides with maximal ordered amphiphilic helical structure (i.e., maximally stabilized amino acid copolymers) can be used for a variety of purposes. For example, transmembrane proteins are notoriously difficult to crystalize. Crystallization is a necessary prerequisite to the determination of atomic structure by X-ray diffraction techniques. Amino acid copolymers (e.g., peptides) having maximally stabilized structure can be used to solubilize transmembranal proteins with helices oriented around the hydrophobic transmembranal section in a fashion permitting formation of crystals which can be analyzed by x-ray diffraction methods (see Schafmeister, C. E., Miercke, L. J. W., and Stroud R. M. 1993, Science 262: 734–737). The stability and thus efficacy of structural analyses of such peptides are enhanced by synthesis according to the method of the invention.

Peptides which have maximal degrees of alpha helicity when adsorbed to hydrophobic surfaces, offer a unique standard for the analysis of degrees of helicity in other peptides or proteins by circular dichroism (CD) or nuclear magnetic resonance (NMR) methods. Thus, amino acid copolymers designed in accordance with the methods disclosed herein are useful in a commercial context as standards for physical measurements based on their high degree of ordered amphiphilic helical structure. Peptides produced according to the methods disclosed herein (or a series of homologous peptides systematically varying stability of alpha-helical structure) permit standardization of such correlations, for example, between several types of NMR chemical shifts and degree of alpha-helicity around individual amino acid residues. Examples of such commercial applications are discussed below.

The determination of the structure of transmembranal proteins by solid state NMR analysis (see Tuzi, S., Naito, A., and Saito, H. 1993, Eur. J. Biochem. 218: 837–844; and Saito, H. and Ando, I. 1989, Ann. Rev. NMR Spectrosc. 21: 209–290), after dehydration of the sample, requires identification of cross peaks in 2D NMR spectra and quantitation of those cross peaks with respect to a standard, such as provided by the peptides designed in accordance with the methods of the invention.

In addition, transmembranal proteins, such as multihelical ion channels or receptor-transducing molecules, cannot alone be crystallized for x-ray crystallography and are too large in vesicles for conventional NMR analyses. Magic angle spin solid state NMR analyses allows acquisition of 2D NMR spectra which can be interpreted in view of spectra of peptides with maximal alpha-helicity (or a series of homologous peptides systematically varying stability of alpha-helical structure) which peptides are designed by the method of the invention.

In another application for use as a commercial standard, peptides with ordered alpha-helical structure designed by methods of the invention allow standardization of CD and NMR measurements of peptide-peptide interactions. Specifically, the peptide PH-1.0 in 50% TFA solution creates a trimeric coiled coil standard to calibrate measurements of such trimeric coiled coil structures which are found in certain proteins.

Peptides designed by the method of the invention for maximal alpha-helicity (or a series of homologous peptides systematically varying stability of alpha-helical structure) can be used as a standard to quantitate the low angle scatter measurements with shape and isotropy of other peptides which are studied with the intention of constructing structural changes which lead to novel biological or catalytic properties.

Aside from utility of the methods disclosed herein for the production of commercial standards for measurement of specific physical properties, amino acid copolymers produced by the methods disclosed herein are practically useful in other contexts. For example, peptides designed according to the method of the invention, when attached to the solid phase of an affinity chromatographic system, adsorb specifically certain circa 70,000 dalton heat shock protein-like molecules and thus permit the efficient purification of such molecules. Specifically, PH-1.0 and homologs may be used for such purifications.

In addition, peptides designed according to the method of the invention demonstrate adsorption of tethered ligands to hydrophobic surfaces. They therefore permit the analysis of the effects of local orientation at the membrane surface of an electron-spin marked group which is tethered at the membrane surface. Adsorption of ligands to hydrophobic surfaces therefore improve solid phase-based methods of immunoassay, such as enzyme-linked immunosorbent assay or radioimmunoassay. Amphiphilic helical peptides which incorporate catalytic functions might also be adsorbed into hydrophobic pores of a membrane permitting efficient catalysis of substrates which are filtered through such membranes.

EXAMPLE 1

Application of the Hydrophobic Strip-of-Helix Template to Known or Putative Helices to Define Categorical Positions with Functional Importance A circular template for a helix with a longitudinal hydrophobic strip was superimposed on the sequences of known or hypothesized helices in amino acid copolymers. The template holds 18 symbols □●△●□○○□●△●□○○□●△○. This generic, helical template corresponds to a sheet projection with successive coils of the helix in slanting columns and with longitudinal quadrants in horizontal rows. By convention, quadrant III has the greatest strip-of-helix hydrophobicity index (SOHHI; the mean hydrophobicity in the Kyte-Doolittle scale of amino acids in □). The infinite template was superimposed on the helical segment 18 times by attaching each of the 18 symbols to the first position in the segment. The overlay with the maximal SOHHI score is chosen.

The distributions of amino acids in longitudinal quadrants were examined with respect to the assignment of residues to one quadrant with the greatest SOHHI (Torgerson et al., 1991, J. Biol. Chem., 266:5521–5524). The amino acid sequences of 247 alpha helices identified in crystallographic structures of 55 proteins by other investigators were placed in the sheet projection of an amphipathic helix to maximize the SOHHI score. In 89% of the 4 and 5 turn helices so examined, the alignment in the crystallographic structures of residues selected to be in the most hydrophobic longitudinal strip closely fit a straight line. The distributions of amino acids in all longitudinal quadrants were then summed over N- and C-termini, interiors, and entire helices (Tables I and II). Hydrophobic amino acids leucine, isoleucine, valine, and phenylalanine were nonrandomly distributed to quadrant III while charged lysine, arginine, aspartate, and glutamate residues were excluded from quadrant III ($p<0.001$ for each amino acid). Selective distributions of other amino acids with respect to longitudinal quadrants were also seen. Termini began in quadrant IV with three nonhydrophobic residues preceding the first leucine, isoleucine, valine, phenylalanine or methionine occurring in the longitudinal hydrophobic strip of quadrant III ($p<0.001$). The last residue of the helix fell in quadrant I with two nonhydrophobic residues following the last leucine, isoleucine, valine, phenylalanine or methionine falling in the longitudinal hydrophobic strip of quadrant III ($p<0.001$).

Two successive ○'s in the template were associated with an empty, first quadrant. These observations demonstrate a dominant role for the extent of the longitudinal hydrophobic strip in regulating the termination of helices, and lead to a refined method to predict termini of helices in proteins. The sharp restriction of leucine, isoleucine, valine and phenylalanine to one longitudinal quadrant also demonstrated that the longitudinal strip is quite narrow on the average and that hydrophobic residues in other quadrants may compete for helix formation.

The distributions of individual amino acids in each quadrant were determined for N- and C-termini, for the interior, and for the entire helix. In accord with Presta and Rose (1988, Science, 240:1632–1641), the left terminus was defined as the first four amino acids of a helix, and the right terminus, the last four amino acids of a helix. The amino acids between the termini constituted the interior of a helix. The template placed the amino acids in 4 quadrants of the sheet projection with 3, 5, 5, and 5 symbols in quadrants I, II, III, and IV of the projection, respectively, so that the null hypothesis distribution assigned a probability of 3/18 for an amino acid being in quadrant I and of 5/18 for being in quadrant II, III, or IV. Since each terminus had four amino acids, only segments with 9 or more amino acids had non-empty interiors. Segments with 3 or fewer amino acids were excluded from analysis. For segments with 4 to 7 amino acids, the N- and C-termini overlapped. The frequency of each amino acid was determined in each quadrant in N- and C-termini, interiors and the entire segment. Table I displays for each amino acid the standardized deviations (the observed proportion minus the expected proportion divided by the standard error) over the four quadrants. Results were separated into 3 levels of significance (p=0.05, 0.01, and 0.001).

TABLE I

N-TERMINUS

| p = 0.001 | Asp | Leu | Ile | | | |
|---|---|---|---|---|---|---|
| I | +3.5 | −2.1 | −2.2 | | | |
| II | +0.3 | −3.2 | −0.4 | | | |
| III | −3.2 | +6.2 | +4.9 | | | |
| IV | +0.1 | −1.2 | −2.7 | | | |
| p = 0.01 | Val | | | | | |
| I | +0.3 | | | | | |
| II | −2.3 | | | | | |
| III | +3.2 | | | | | |
| IV | −1.1 | | | | | |
| p = 0.05 | Gln | Glu | Lys | Phe | | |
| I | −1.0 | +0.1 | −0.2 | −1.4 | | |
| II | +1.9 | +2.1 | +0.2 | −2.0 | | |
| III | −2.3 | −2.9 | −2.8 | +2.3 | | |
| IV | +1.3 | +0.7 | +2.7 | +0.9 | | |

INTERIOR

| p = 0.001 | Asp | Ile | | | | |
|---|---|---|---|---|---|---|
| I | +3.4 | −1.2 | | | | |
| II | +1.7 | −2.2 | | | | |
| III | −2.8 | +4.4 | | | | |
| IV | −1.8 | −0.9 | | | | |
| p = 0.01 | Thr | Phe | | | | |
| I | +1.9 | −1.6 | | | | |
| II | +2.3 | −0.7 | | | | |
| III | −1.5 | +3.5 | | | | |
| IV | −2.7 | −1.6 | | | | |
| p = 0.05 | Asn | Gln | Lys | Arg | Leu | Val |
| I | +0.9 | +2.6 | +1.5 | −0.5 | −2.5 | −2.2 |
| II | −0.9 | −0.5 | +1.1 | +0.2 | −0.1 | −0.8 |
| III | −2.4 | −2.3 | −2.8 | −2.6 | +2.7 | +2.4 |
| IV | +2.5 | +0.7 | +0.6 | +2.9 | +0.5 | −0.2 |

C-TERMINUS

| p = 0.001 | Leu | Val | Ile | | |
|---|---|---|---|---|---|
| I | −2.7 | −1.9 | −2.0 | | |
| II | −2.2 | −2.2 | −1.3 | | |
| III | +5.6 | +5.2 | +4.2 | | |
| IV | −1.1 | −1.6 | −1.3 | | |
| p = 0.01 | Asn | Asp | Lys | Phe | |
| I | +2.9 | +3.0 | +1.3 | −1.2 | |
| II | +0.9 | +0.4 | +0.6 | −1.5 | |
| III | −2.2 | −2.7 | −3.4 | +3.9 | |
| IV | −1.0 | −0.1 | +1.7 | −1.5 | |
| p = 0.05 | Glu | Arg | | | |
| I | +1.0 | +2.3 | | | |
| II | +1.2 | −0.2 | | | |
| III | −2.8 | −2.2 | | | |
| IV | +0.7 | +0.4 | | | |

TABLE II

ENTIRE HELIX

| p = 0.001 | Asp | Glu | Lys | Arg | Leu | Val |
|---|---|---|---|---|---|---|
| I | +5.5 | +0.7 | +1.4 | +0.4 | −3.9 | −2.2 |
| II | +1.2 | +1.9 | +1.1 | +0.6 | −3.4 | −2.9 |
| III | −4.8 | −4.4 | −5.1 | −3.8 | +7.7 | +6.1 |
| IV | −1.0 | +1.9 | +2.9 | −2.8 | −1.1 | −1.4 |
| p = 0.001 | Ile | Phe | | | | |
| I | −3.1 | −2.4 | | | | |
| II | −2.3 | −2.2 | | | | |
| III | +7.8 | +5.9 | | | | |
| IV | −2.8 | −1.6 | | | | |
| p = 0.01 | Asn | Gln | | | | |
| I | +2.5 | +1.2 | | | | |
| II | +0.5 | +1.5 | | | | |
| III | −3.7 | −4.0 | | | | |
| IV | +1.1 | +1.5 | | | | |
| p = 0.05 | Thr | Tyr | | | | |
| I | +1.9 | +0.1 | | | | |
| II | +1.4 | +1.4 | | | | |
| III | −2.9 | −3.2 | | | | |
| IV | −0.1 | +1.7 | | | | |

In Tables I and II, the observed set of frequencies for the four quadrants were compared to the null distribution by means of the Chi-square goodness-of-fit test on 3 degrees of freedom and the results were verified with the likelihood ratio test. The null probability distribution assigned 3/18 to quadrant I and 5/18 to quadrants II, III, and IV. To indicate possible false rejection of the null hypothesis, results were distinguished with p-values of 0.05, 0.01, and 0.001. With p=0.001 and 50 independent tests, a type I error occurs 5% of the time using a Bonferroni correction for multiple comparisons. For each quadrant within a statistically significant distribution of frequencies, the deviation from the expected proportion, p, was standardized using the quantity (observed frequency−p)/SE where SE was the standard error under the binomial model, $[p(1-p)/n]^{0.5}$ and n was the number of times the amino acid occurred. The standardization was used because the difference in proportions can be misleading. For example, if one amino acid appeared in quadrant I twenty out of forty times while a rarer amino acid appeared in quadrant I two out of four times, both would have observed deviations of 50-17=33%.

EXAMPLE 2

Comparison of the Longitudinal, Hydrophobic Strip Identified in Primary Sequences of Helices Against Known Helix Structures in Crystallized Proteins Predicted quadrant orientations approximated crystallographic structures well. Projections of the crystallographic co-ordinates of the α-carbon chain tracings were viewed along the helical axis, using the Quanta program of Polygen Corporation on a Silcon Graphics 4D/70GT computer system. From the geometric center of the helical projection, radii were drawn to quadrant III residues (□). The maximal sector angle was the absolute value of the greatest angle among those radii. The mean sector angle was the average of the absolute values for the angles between the most clockwise radius and the other radii. The structural relevance of the template-fitting model of alpha helices was tested by direct examination of all 4- or 5-turn helices in 7CAT, 5CPA, 2CYP, 4LDH, 2MBN, 1MBO, and 2SNS for alignment of the residues predicted to fall in the axial hydrophobic strip of quadrant III (Torgerson et al., 1991, *J. Biol. Chem.* 266:5521–5524). Projections of x-ray crystallographic coordinates for 22 of 28 helices demonstrated a maximal sector angle among residues in the axial hydrophobic strip of 99° and a mean sector angle of 61° (Table III). Table III shows sectors of residues in 4- or 5-turn axial hydrophobic strips. The assignments of amino acid residues to four quadrants, based on positioning of recurrent hydrophobic residues in one axial strip to maximize the SOHHI, closely matched crystallographic measurements.

TABLE III

| | Maximum Sector | Mean Sector |
|---|---|---|
| Presta and Rose Helices | | |
| 5CPA 15–28 | 66 | 53 |
| 5CPA 74–89 | 77 | 43 |
| 5CPA 216–230 | 77 | 57 |
| 1MBO 4–17 | 79 | 63 |
| 1MBO 21–35 | 70 | 48 |
| 1MBO 59–76 | 90 | 56 |
| 1MBO 83–95 | 67 | 52 |
| 1MBO 101–118 | 60 | 38 |
| Richardson and Richardson Helices | | |
| 7CAT 53–67 | 124 | 101 |
| 7CAT 258–271 | 65 | 42 |
| 7CAT 437–450 | 149 | 120 |
| 7CAT 470–485 | 99 | 62 |
| 7CAT 485–500 | 59 | 55 |
| 5CPA 14–30 | 94 | 62 |
| 5CPA 173–187 | 78 | 53 |
| 2CYP 42–55 | 63 | 51 |
| 2CYP 103–120 | 180 | 94 |
| 2CYP 164–177 | 75 | 69 |
| 4LDH 30–44 | 119 | 74 |
| 4LDH 55–70 | 73 | 61 |
| 4LDH 141–154 | 94 | 53 |
| 4LDH 165–181 | 69 | 48 |
| 4LDH 247–264 | 72 | 56 |
| 2MBN 20–37 | 120 | 65 |
| 2MBN 82–98 | 137 | 95 |
| 2MBN 100–116 | 65 | 42 |
| 2SNS 54–69 | 52 | 31 |
| 2SNS 121–136 | 72 | 60 |

EXAMPLE 3

Termination of Helices with Three Nonhydrophobic Residues at the N-Terminus and Two Nonhydrophobic Residues at the C-Terminus The quadrants for the terminations of helices are presented in Table IV. A helix was more likely to start in quadrant IV with 3 residues preceding the hydrophobic one in quadrant III. The N-terminus was more likely to be an untethered loop. The last amino acid was more likely to be in quadrant I, two amino acids after the hydrophobic axial strip and was less likely to end in the hydrophobic strip. The standardized deviations of the frequencies of first and last residues of the helices are presented for each axial quadrant of their appearances, $p \leq 0.001$.

TABLE IV

| TERMINI OF HELICES | | |
|---|---|---|
| | Presta and Rose | Richardson and Richardson |
| Beginnings | | |
| I | –3.5 | –6.6 |
| II | –3.2 | –3.6 |
| III | –0.9 | +1.7 |
| IV | +7.0 | +7.4 |
| Endings | | |
| I | +7.5 | +11.4 |
| II | +1.5 | +2.8 |
| III | –2.4 | –4.4 |
| IV | –5.3 | –8.0 |

EXAMPLE 4

Identification of Unique Structure of Helix Termini

An α-helix terminates when the virtual extension of its most hydrophobic, longitudinal strip containing leucine, isoleucine, valine, phenylalanine, and methionine lacks those residues. The hydrophobic strip-of-helix template was applied to each of 247 helices and the template was extended into sequences beyond the ends of the helices. Leucine, isoleucine, valine, phenylalanine, and methionine occurred in □ positions in the longitudinal strip-of-helix at an increased frequency (p<0.001), but in the first and second □ positions beyond either end of each true helix, they occurred at the same frequency as for their empirical distribution over all the proteins. Helices terminate when the longitudinal hydrophobic strip is not extended.

Frequencies of amino acids were determined in □ positions and in intervening loops (○, ●, and Δ positions between the □) for 247 helices and their virtual extensions in 55 crystallized proteins (Table V). Table 5 shows the distributions of amino acids in the longitudinal hydrophobic strip □ and in intervening loops (○, ●, and Δ) in 252 α-helices (real) and in parahelical segments extended in virtual helical configurations (virtual). The virtual extensions were the template assignments in the parahelical regions extending the pattern assigned to the helix itself. The first and second virtual □ positions would have occurred in the longitudinal hydrophobic strip were the helix extended. In the N- and C-terminal □ positions of true helices, the frequencies of leucine, isoleucine, valine, phenylalanine, or methionine substantially exceeded those predicted for an empirical distribution of amino acids for all the proteins (p<0.001). Charged amino acids were suppressed in the terminal □ positions of the true helices. The frequencies of leucine, isoleucine, valine, phenylalanine, or methionine in the first and second □ positions in each virtual extension of the helix fell to the level predicted from the null hypothesis, i.e., that the empirical distribution over the entire set of proteins determined the frequencies. The placement of leucine, isoleucine, valine, or phenylalanine in recurrent positions in the primary sequence determines the formation of an α-helix with a longitudinal strip, when the longitudinal hydrophobic strip can stabilize helical nucleation against a hydrophobic surface (Torgerson et al., 1991, *J. Biol. Chem.*, 266:5521–5524). This finding demonstrates that the absence of a hydrophobic residue in the extension of that strip fails to anchor the next successive loop and thus dictates termination of the helix. In Table V, the distributions of amino acids in the first proximal virtual loop and second proximal virtual strip in both N- and C-terminal parahelical segments were uniformly at the frequency of the uniform distribution of amino acids in proteins and were not reported in the table.

TABLE V

| | N-TERMINUS | | | C-TERMINUS | | |
|---|---|---|---|---|---|---|
| | VIRTUAL | REAL | | REAL | | VIRTUAL |
| | STRIP | LOOP | STRIP | STRIP | LOOP | STRIP |
| L | — | −2.1 | +5.0 | +9.6 | −2.6 | — |
| I | — | −2.4 | +4.2 | +5.5 | −3.0 | — |
| V | — | −3.0 | +4.1 | +5.6 | −4.1 | — |
| F | — | −3.1 | +2.5 | +4.1 | −2.8 | −2.8 |
| M | — | −2.2 | +2.2 | +3.1 | — | — |
| D | — | +4.9 | — | −3.3 | — | — |
| E | — | +4.1 | — | −3.3 | — | — |
| H | — | — | — | +2.0 | +2.0 | — |
| R | — | — | −2.9 | −2.6 | — | +2.9 |
| K | — | — | −2.9 | −3.2 | +4.5 | +2.4 |
| A | — | — | — | — | — | — |
| C | — | — | — | — | — | — |
| G | — | — | — | — | — | — |
| N | — | +2.1 | — | −3.1 | — | — |
| P | — | — | — | −3.2 | — | — |
| Q | — | — | — | −2.8 | +2.1 | — |
| S | — | — | — | −2.1 | — | — |
| T | — | −2.2 | — | −2.5 | — | — |
| W | — | — | — | — | — | — |
| Y | — | — | — | — | — | — |

EXAMPLE 5

Definition of Helix-Stabilizing Residues and Their Unique Positions with Respect to the Hydrophobic Strip-of-Helix Template The excess frequency of several amino acids differed significantly at N- versus C-termini of α-helices (Table V). Aspartate and glutamate were increased in frequency in the N-terminal loop of the real helix. Lysine and histidine were increased in the C-terminal loop of the real helix, and arginine and histidine were increased in the C-terminal first virtual □ position. The distributions of these amino acids otherwise approximated the empirical distribution model for the remainder of the helix, except in □ positions where they were excluded. The negative residues aspartate and glutamate stabilize the helix N-terminal macrodipole δ+ charge in the native protein (Hol et al., 1981, *Nature* 294:532–536). The positive residues histidine, lysine, and arginine stabilize the helix C-terminal macrodipole δ− charge. Asparagine was also more frequent in the N-terminal loop, forming a hydrogen bond to the peptidyl backbone to initiate the helix.

EXAMPLE 6

Structure of Residues Within the Longitudinal Hydrophobic Strip-of-Helix

The hydrophobic strip is narrow. While most leucine, isoleucine, valine, phenylalanine, and methionine residues in helices fell in the longitudinal hydrophobic strip with the greatest strip-of-helix hydrophobicity index (Torgerson et al., 1991, *J. Biol. Chem.*, 266:5521–5524), the distribution of these hydrophobic residues in the remainder of the helix was examined. The residues in the hydrophobic strip do not fall precisely in a straight line. Some of the positions in quadrants II and IV, the "strip interdigitating positions", fall closely along quadrant III. The distribution of leucine, isoleucine, valine, phenylalanine, and methionine was examined in these strip bordering positions of quadrants II and IV and in the remainder of quadrants I, II and IV (Table VI). Leucine, isoleucine, valine, phenylalanine, and methionine were restricted to □ and excluded from ● as well as from ○ and Δ; there was no tendency for broadening of the longitudinal hydrophobic strip. Aspartate, glutamate, and lysine were found in ○ and Δ positions while histidine and arginine occurred in ●. Asparagine was more often in ●; proline, glutamine and threonine, in Δ; and tyrosine in ● but not ○.

TABLE VI

Longitudinal distributions of amino acids in α-helices.

| | □ | ● | ○ | Δ |
|---|---|---|---|---|
| L | +12.9 | −4.1 | −4.4 | −5.5 |
| I | +10.0 | −4.0 | −2.8 | −3.9 |
| V | +9.7 | −3.4 | −3.2 | −3.9 |
| F | +8.2 | — | −3.6 | −3.6 |
| M | +1.7 | — | — | — |
| D | −5.3 | — | +4.1 | — |
| E | −6.1 | — | +2.3 | +3.0 |
| H | +3.0 | — | — | — |
| K | −7.1 | — | +2.6 | +4.4 |
| R | −5.1 | +3.3 | — | — |
| A | — | — | — | — |
| C | +2.2 | — | — | — |
| G | −2.4 | — | — | — |
| N | −5.1 | — | +3.1 | — |
| P | −3.0 | — | — | +2.3 |
| Q | −4.8 | — | — | +2.2 |
| S | −2.5 | — | — | — |
| T | −2.8 | — | — | +3.5 |
| W | — | — | — | — |
| Y | — | +4.7 | — | — |

A "hydrophobicity break" in the hydrophobic strip-of-helix was defined as the single amino acid in the strip with minimal hydrophobicity. The distributions of amino acids in that position, and in the adjacent (n−2, n−1, n+1, n+2) positions along the longitudinal hydrophobic strip were scored (Table VII). Histidine and tryptophan were frequently present in the "break" and both positions in the longitudinal hydrophobic strip adjacent to the "break" held increased frequencies of leucine, isoleucine, valine, and phenylalanine (each, $p<0.001$) and methionine ($p<0.01$). This demonstrates that longitudinal hydrophobic strip-of-helix sequences can be interrupted by a single nonhydrophobic residue. However, two successive non-(leucine, isoleucine, valine, phenylalanine, or methionine) residues in the strip-of-helix terminate the helix. This observation may help to locate helix termini by searching for a motif of hydrophobic residues occurring in terminal □ but not in the two, next virtual □ positions in the extension of the longitudinal hydrophobic strip.

TABLE VII

Distributions amino acids in □ positions of a longitudinal hydrophobic strip centered on the least hydrophobic residue.

|   | -2 | -1 | BREAK | +1 | +2 |
|---|---|---|---|---|---|
| L | +4.8 | +4.8 | 0 | +7.0 | +6.4 |
| I | +4.8 | +5.2 | 0 | +6.7 | +3.9 |
| V | +3.7 | +3.9 | 0 | +5.1 | +4.5 |
| F | — | +2.9 | 0 | +2.1 | +5.9 |
| M | — | +2.2 | 0 | — | — |
| D | — | -2.2 | — | -2.7 | -2.3 |
| E | — | -2.5 | — | -2.3 | -2.6 |
| H | — | — | +3.9 | — | — |
| K | -2.1 | +2.7 | — | -3.3 | -2.9 |
| R | — | — | — | -2.2 | — |
| A | — | — | — | — | — |
| C | — | +2.1 | — | +2.5 | — |
| G | — | — | — | — | — |
| N | — | — | -2.4 | -2.2 | — |
| P | — | — | — | — | — |
| Q | — | — | — | -2.2 | — |
| S | — | — | — | -2.6 | — |
| T | — | — | — | — | -2.1 |
| W | — | — | +2.2 | — | — |
| Y | — | — | — | — | — |

*The longitudinal hydrophobic strips of 247 helices were aligned on the least hydrophobic residue other than leucine, isoleucine, valine, phenylalanine or methionine. Within the longitudinal hydrophobic strip, amino acids in the positions adjacent to the least hydrophobic residue were usually Leu, Ile, Val, Phe or Met.

EXAMPLE 7

Identification of Structure of Crossing Alpha-Helices and Method to Stabilize or Alter the Structure of Such Crossing Regions The orientation of crossing α-helices was tested with respect to their respective longitudinal strips. In crossing regions of helices, the circumferential breadth of the hydrophobic strip and the relative frequencies of both small and charged amino acids of that strip in crossing regions between helices were analyzed. The local organization of hydrophobicity or other consensus structures on a longitudinal surface of a helix may determine the crossing points of packed helices. For example, small residues in the hydrophobic strip may determine the positions of preferred crossing regions (as do notches in a log), and the hydrophilicity of charged residues may warrant exclusion from these hydrophobic crossing regions.

For the analysis of crossing helices, fifteen proteins were studied with the Quanta program of Polygen Corp. on a Silicon Graphics 4D/70 GT computer system. Cα backbone projections were displayed with coordinates and helix lengths from the Brookhaven Protein Data Bank (protein codes: 1ECA, 1LYZ, 1MBO, 1RHD, 1SBT, 2ACT, 2LDX, 2LZM, 2SNS, 3C2C, 3PGK, 3TLN, 4TNC, 5CPA, 7CAT). The analysis of 13 pairs of packed helices previously studied by Lesk et al. (1980, *J. Mol. Biol.*, 136:225–270) showed that the minimal distances between Cα's of two crossing helices were less than 7.5 Å. For all residues in crossing helices which were no more than 7.5 Å apart, we measured distances from each residue's Cα to the Cα's of neighboring helices. Such measurements were characterized with respect to residues being in □, ●, ○, Δ, and ● positions of the strip-of-helix template assignment (Reyes et al., 1989, *J. Biol. Chem.*, 264:12854–12858; Torgerson et al., 1991, *J. Biol. Chem.*, 266:5521–5524).

A crossing region was defined. Two α-helices were defined as crossing if there was at least one pair of Cαs whose interhelical distance was less than 7.5 Å. Such a measurement was called the Limiting Interhelical Alpha-carbon Distance (LIAD). In parallel to the method of Chothia et al. (Chothia et al., *J. Mol. Biol.* 145:215, 1981) to measure multiple residue interactions at the closest point of approach between the two helices, the three shortest LIADs were determined without restricting their lengths as long as the shortest was less than 7.5 Å. The pair of amino acids determining a LIAD was called the LIAD pair. Individual amino acids in a helix could occur in more than one LIAD pair. The crossing region was defined to include those amino acids on one helix in the shortest three LIAD pairs. The magnitude of the LIAD is not correlated with the residue volumes of the amino acids forming the shortest LIAD (correlation r=0.44). Single-loop helices or helices with LIAD pairs involving only the terminal two residues were excluded because they usually only approached but did not cross another helix. 86 helices in fifteen proteins had 74 pairs of adjacent α-helices with crossing regions.

The rotational orientation between α-helices was determined with respect to crossing longitudinal hydrophobic strips. Amino acids in crossing regions frequently also lay in longitudinal hydrophobic strips (z=+5.1; p<0.001). The frequency with which longitudinal hydrophobic strips in neighboring helices intersected each other, i.e., the helices crossed through their longitudinal hydrophobic strips (Table VIII), was determined. Crossing between hydrophobic strips occurred when at least one LIAD, termed the strip-to-strip LIAD, had both amino acids of the LIAD pair in hydrophobic strips of their respective helices (Table V). The longitudinal hydrophobic strips-of-helix frequently face each other, Several amino acids were significantly included in or restricted from crossing regions (Table VIII). Hydrophobic amino acids leucine, isoleucine, valine, phenylalanine, and methionine as a group occurred more frequently in crossing regions (z=+6.4; p<0.001). In contrast, both negatively charged amino acids aspartate and glutamate (z=−4.2) and positively charged amino acids histidine, lysine, and arginine (z=−4.4) were excluded from crossing regions (each set, p<0.001). The individual amino acids most often included in crossing regions were valine and isoleucine (each, p<0.001); Ala was significant as well (p<0.01). For the charged amino acids, lysine and aspartate were the most highly excluded (each, p<0.001). Excepting histidine, threonine, and cysteine, our distributions did not differ significantly from those of Chothia et al. (1981; *J. Mol. Biol.*, 145:215–250).

The distributions of charged amino acids in the longitudinal hydrophobic strip was determined with respect to occurrence in crossing regions. 92% of aspartate, glutamate, histidine, lysine, and arginine in such strips did not fall in a crossing region ($X^2$ for equal proportions=6.8; p<0.01). The smallest amino acid was also determined the "size break", in each longitudinal hydrophobic strip (Table IX). Chothia et al. (1981, *J. Mol. Biol.*, 145:215–220) reported generally that of smaller amino acids were packed along larger ones at helical crossings. In this analysis, the smallest residue in the strip fell in the crossing region 46% of the time, and 59% of the crossing regions with a strip-to-strip LIAD pair contained at least one "size break". Overall, 49% of the smallest amino acids in all longitudinal hydrophobic strips fell in crossing regions ($X^2$=4.8; p<0.05). Within crossing regions, no broadening of hydrophobicity around the longitudinal hydrophobic strip occurred. The frequencies of hydrophobic residues and crossing regions involving strip interdigitating ● positions were tested. There was no increase in the frequency of leucine, isoleucine, valine, phenylalanine, or methionine in ● positions which occurred in crossing regions versus positions not in crossing regions ($X^2=0.5$; $p>0.05$).

TABLE VIII

Distributions of amino acids in crossing regions of α-helices.

| | # observed | % observed | % expected | Z (here) | Z (Chothia) |
|---|---|---|---|---|---|
| L | 53 | 11.7 | 9.6 | — | — |
| I | 47 | 10.4 | 4.8 | +5.7 | +4.0 |
| V | 54 | 11.9 | 6.6 | +4.6 | +4.0 |
| P | 21 | 4.6 | 4.8 | — | — |
| M | 14 | 3.1 | 2.5 | — | — |
| D | 10 | 2.2 | 6.2 | −3.5 | −2.2 |
| E | 22 | 4.9 | 7.6 | −2.2 | −3.3 |
| H | 4 | 0.9 | 2.7 | −2.4 | +2.1 |
| R | 16 | 3.5 | 3.6 | — | — |
| K | 13 | 2.9 | 8.2 | −4.2 | −2.6 |
| A | 71 | 15.7 | 11.5 | +2.9 | — |
| C | 7 | 1.5 | 2.1 | — | −5.1 |
| G | 31 | 6.9 | 4.9 | — | — |
| N | 11 | 2.4 | 3.9 | — | — |
| F | 10 | 2.2 | 2.3 | — | — |
| Q | 11 | 2.4 | 3.7 | — | — |
| S | 27 | 6.0 | 5.7 | — | — |
| T | 10 | 2.2 | 4.9 | −2.6 | — |
| W | 6 | 1.3 | 1.3 | — | — |
| Y | 14 | 3.1 | 2.9 | — | — |

Distributions of amino acids were calculated in crossing regions defined by the shortest three LIADs between helices when at least one LIAD was less than 7.5 Å. 452 residues in 74 crossing regions were counted, including a fourth LIAD for four crossing regions which had two pairs of amino acids tying for third closest LIAD. The expected percentages were calculated from the distribution of 3661 amino acids in 257 α-helices. Z scores were also computed from the data of Chothia et al. (1981, *J. Mol. Biol.*, 145:215–250). For groups of amino acids Z scores were: leucine, isoleucine, valine, phenylalanine, and methionine, +6.3; arginine, histidine, and lysine, −4.4; aspartate and glutamate, −4.2. These observations demonstrate that the smallest residue, especially alanine or valine in a longitudinal, hydrophobic strip-of-helix is predictably at the crossing region between adjacent helices and that charged residues in the hydrophobic strip-of-helix are not in the crossing region.

TABLE IX

Distribution of amino acids in □ positions at and adjacent to size breaks within the longitudinal hydrophobic strips of crossing helices.

| | −1 | Break | +1 |
|---|---|---|---|
| L | +4.2 | — | +2.9 |
| I | +4.9 | — | +5.8 |
| V | +4.2 | +4.5 | +3.4 |
| F | — | −2.1 | +3.4 |
| M | +3.3 | — | — |
| D | — | — | −2.1 |
| E | −2.1 | — | −2.3 |
| H | — | — | — |
| R | — | −2.8 | −2.1 |
| K | — | — | — |
| A | −2.2 | +6.5 | — |
| C | — | — | — |
| G | — | — | — |
| N | — | — | — |
| P | — | — | — |
| Q | — | — | — |
| S | — | — | — |
| T | — | — | — |
| W | — | — | — |
| Y | — | — | — |

The 86 longitudinal hydrophobic strips were aligned on the residue with the smallest volume on the scale of Chothia (1975, *Nature*, 254:304–308). When identical amino acids were smallest, the selected amino acid was the one with the largest neighbors. The two most frequently smallest amino acids were alanine and valine (each $p<0.001$). Within the longitudinal hydrophobic strip the positions next to the size break were usually leucine, isoleucine, valine, phenylalanine and methionine.

EXAMPLE 8

Confirmation of the Mechanism for Helix Stabilization

To test further the idea that a narrow, longitudinal strip-of-helix promotes coiling of helices on hydrophobic surfaces, a series of known T cell-presented peptides were synthesized and their coiling on lipid vesicles was analyzed by circular dichroism (Lu et al. 1990, *J. Immunol.* 145:899–904). There was a modest correlation between SOHHI and the degree of helicity ($r=0.77$; $p=0.07$). Similar studies on coiling of T cell-presented peptides in trifluoroethanol or sodium dodecyl sulfate have been reported by others, coming to the same conclusion but without a systematic analysis of the role of the hydrophobic strip-of-helix in such binding (Vita et al. 1990, *Molec. Immunol.* 27:291–295; Lark et al. 1989, *Peptide Res.* 2:314–321). In order to evaluate specifically the effect of number and placement of aliphatic, hydrophobic residues of the longitudinal hydrophobic strip on helical coiling, prototypic helix peptide PH-1.0 (leucine-tyrosine-glutamate-leucine-glutamine-lysine-leucine-threonine-glutamine-threonine-leucine-lysine) SEQ ID NO: 1) and a series of its analogs replacing one or two leucine residues with threonine were synthesized (Lu et al. 1991, *J. Biol Chem.* 266:10054–10057). While all of these analogs coiled as helices from 28 to 57% in the presence of trifluoroethanol, appreciable helicity in the presence of lipid vesicles was found only for analogs with three adjacent leucines in the longitudinal hydrophobic strip and for one analog with two adjacent leucines on cycles also joined by the salt bridge glutamate$^4$-lysine$^7$. These experiments demonstrate that adsorption and helical coiling on lipid membranes depends upon a cooperative effect of hydrophobic residues forming a longitudinal hydrophobic strip in terms of the number and placement of hydrophobic residues.

This general method of analysis, based first on a consensus pattern of hydrophobicity, may also be applied to the study of β-sheets and turns. The regulating principle may be the generation of a local structure with a hydrophobic surface containing multiple hydrophobic residues which are adjacent in the folded structure but separated in the primary sequence in patterns which may form characteristic motifs. The strength of the local, secondary structure may be reflected in the mean hydrophobicity of the residues in the motif of the hydrophobic surface. For example, hydrophobic residues in particular patterns around prolines may characterize some β-turns and the alternating hydrophobicity of β-strands can be identified. The principles of this study may also be used to predict docking of secondary structural elements to form tertiary structures in proteins.

TABLE X

Helicity of PH-1.0 and its Analogs*

| Peptide | TFE Solution | | Lipid Vesicles | |
|---|---|---|---|---|
| | $\Theta_{222\ nm}$ | % Helicity | $\Theta_{222\ nm}$ | % Helicity |
| PH-1.0 | −16,543 | 57 | −9,607 | 33 |
| PH-1.1 | −10,710 | 37 | −5,531 | 19 |
| PH-1.2 | −10,630 | 37 | −5,531 | |
| PH-1.3 | −8,633 | 30 | −3,760 | |
| PH-1.4 | −8,305 | 29 | −7,903 | 27 |
| PH-1.5 | −8,206 | 28 | −5,123 | |
| PH-1.6 | −8,726 | 30 | −2,702 | |
| PH-1.7 | −9,894 | 34 | −4,046 | 14 |
| PH1.10 | −8,550 | 29 | −5,796 | |
| PH-4.2 | −9,179 | 32 | −4,053 | 14 |

TABLE XI

Restricted Distribution of Amino Acids in and near alpha helices in positions defined with the hydrophobic strip-of-helix template

| Amino Acids | N-Loop | N-☐ | C-☐ | C-Loop | C-virt ☐ |
|---|---|---|---|---|---|
| Leucine, Isoleucine, Valine, Phenylalanine, Methionine | −7.2 | +8.2 | +13.4 | −8.2 | −2.1 |
| Aspartate, Glutamate | +6.6 | −2.1 | −4.8 | — | — |
| Lysine, Arginine | — | −4.2 | −4.2 | +4.2 | +3.7 |
| Histidine | — | — | +2.0 | +2.0 | — |
| Asparagine | +2.1 | — | −3.1 | — | — |
| Glutamine | — | — | −2.8 | +2.1 | — |

In Table X, percentage helicity of peptides with CD spectra of α-helices was calculated from −Θ$_{222\ nm}$ values (units: deg cm$^2$ dmol$^{-1}$) and peptide concentration according to Taylor and Kaiser (1987, *Meth. Enzymol.*, 154: 473) using maximal values of Bradley et al., 1990, *J. Mol. Biol.* 215: 607). For analog peptides, CD spectra were taken at 25° C. with peptides in 0.01M phosphate buffer, pH 7.0, with 45% TFE or at 4° C. in that buffer with lipid vesicles.

EXAMPLE 9

Prediction of Structural Helices by Application of the Hydrophobic Strip-of-Helix Template Distribution of amino acids were determined in positions in and around α-helices in positions defined with the hydrophobic strip-of-helix template. The distributions of amino acids over ☐ and ○ positions of the hydrophobic strip-of-helix template were determined (Vasquez et al., 1992, *J. Biol. Chem.* 268: 7406) and Z values for distributions of groups of amino acids (leucine, isoleucine, valine, phenylalanine and methionine; aspartate and glutamate; arginine, histidine and lysine; asparagine, glutamine) were calculated (Table XI). The distributions were so significantly different from the uniform distribution of the residues across the proteins that it can be concluded that they reflected functions of the side chains in stabilizing the helices. Contributions to the prediction of α-helices of the finding of characteristic distributions of residues in and about the α-helices were tested. In Table XI, absolute values of Z greater than 3.6 correspond to p<0.0001; greater than 3.1, p<0.001; greater than 2.3, p<0.01; greater than 1.6, p<0.05. Values not significant at p<0.05 are indicated by −. N-loop are the N-terminal residues in the α-helix preceding the first ☐ position (N-☐) in the helix. C-loop are the C-terminal residues in the α-helix following the last ☐ position (C-☐) in the helix. C-virt. ☐ is the first ☐ position following the helix determined by extension of the strip-of-helix template into the parahelical sequence.

The predictor algorithm was based upon templates ○○○☐○○○☐○○☐○○ and ○○○☐○○☐○○○☐○○ which included 3 turns through the hydrophobic strip in an α-helical pattern. They are segments of an 18-member template (☐○○○☐○○☐○○○☐○○☐○○○) required to return an α-helical pattern to 0°. That is, if each successive residue adds 100°, i.e., 100°, 200°, 300°, 40°, 140°, etc., it requires 19 residues to return to 0° exactly. ○○○ was added to the N-terminus and ○○ to the C-terminus because those additional positions were usually found in α-helices; appended to the respective terminal, ☐ is in the longitudinal strip-of-helix (p<0.001) (Torgerson et al., 1991, *J. Biol. Chem.*, 266:5521–5524). That is, helices did not end in ○ positions in the longitudinal strip but instead with three ○ positions at the N-terminus and two ○ positions at the C-terminus, on the average. Template assignments scored positive when the mean hydrophobicity of residues in ☐ positions was greater than 3.0 on the Kyte-Doolittle scale. Practically, this usually required all three ☐ positions to come from the group of amino acids (with hydrophobicity indices): leucine (3.8), isoleucine (4.5), valine (4.2), phenylalanine (2.8), and methionine (1.9). The effect of lowering the hydrophobicity threshold for positive scoring of the template is seen in Table XII. Overlapping predictions were merged when the presence of amino acids in restricted distributions described in Table XI was scored. When a region of overlapping template predictions was found, the entire sequence was taken from a putative helix and evaluated with the method described in Example I.

The sensitivity and efficiency of α-helix predictions were determined with only the hydrophobic strip-of-helix template and with addition of certain residue-position patterns (Table XIII) (Vasquez et al., 1992, *J. Biol. Chem.* 268: 7406). The sensitivity and efficiency of the predictor algorithm based on ○○○□○○○□○○□○○ and ○○○□○○□○○○□○○ templates was better than with a previous 4-turn template (□○○○□○○□○○○□) in which the pattern terminated with □ positions, and alternate placements of ○○○ vs ○○ loops within the template was not an option (Reyes et al., 1989, *J. Biol. Chem.*, 264:13854-12858). The current method was also superior to the Chou-Fasman and Garnier-Osguthrope-Robson methods embodied in a DNA* program. Addition of the requirement for finding of aspartate or glutamate in N-terminal ○ positions; or histidine, lysine, arginine at C-terminal ○ or first parahelical □ positions had a marginal (not significant) improvement in efficiency and a loss in sensitivity. The loss in sensitivity (number helical identified/total number of helices) was expected since only a fraction of the helices had such macrodipole-stabilizing residues. This program scored the presence of helix-stabilizing residues in certain positions, and constituted the most sensitive and efficient method available to predict α-helices from primary sequence. It is slso an essential step toward the development of docking algorithms which will permit better predictions in the future based upon analysis of fittings of locally ordered structures identified with this invention.

TABLE XII

Sensitivity (Sens.) and Efficiency (Eff.) of Template Predictions

| Mean Hydrophobicity of □ positions, ≦ | All Helices | | Helices ≧ 8 Residues | |
|---|---|---|---|---|
| | Sens. | Eff. | Sens. | Eff. |
| 3.5 | 0.26 | 0.37 | 0.30 | 0.37 |
| 3.0 | 0.36 | 0.42 | 0.42 | 0.42 |
| 2.5 | 0.29 | 0.32 | 0.34 | 0.32 |
| 2.0 | 0.16 | 0.20 | 0.18 | 0.20 |
| 1.5 | 0.06 | 0.11 | 0.07 | 0.11 |

TABLE XIII

Categorical Positions in and around alpha helices as defined with the hydrophobic strip-of-helix template

| | Sensitivity | Efficiency |
|---|---|---|
| Template Only | .36 | .42 |
| Template and D, E at N-term. | .15 | .47 |
| Template and H, K, R at C-term. | .22 | .49 |
| Template and N at N-term. | .05 | .41 |
| Template and Q at C-term. | .02 | .15 |
| Template and D, E, at N-term. or H, K, R at C-term. | .28 | .49 |
| D, E, at N-term. and H, K, R at C-term. | .09 | .48 |
| E at N-term. or H, K, R at C-term. or N at N-term. | .34 | .49 |

EXAMPLE 10

Demonstration that Positions in the Strip-of-Helix are Sensitive to Function-Loss Mutation The sensitivity of bacteriophage T4 lysozyme function to amino acid substitutions at defined positions in and around the longitudinal, hydrophobic strips of 9 α-helices was assessed after systematic replacement of each residue in the protein with a series of 13 amino acids. The hydrophobic strips were defined by identifying the longitudinal sectors in the helices with the highest mean residue hydrophobicities. Sensitivity to mutation (the percentage of replacements leading to loss of function) was calculated for each residue in the following positions: whole protein, helices, hydrophobic strips, other positions within the helices, and various positions within the hydrophobic strips as well as their extensions beyond the helices.

Application of the hydrophobic strip-of-helix-identifying algorithm to the 9 α-helices of T4 lysozyme demonstrated sensitivities to amino acid replacements in certain positions identified with the strip-of-helix hydrophobicity template (Rennell et al., 1992, *J. Biol. Chem.*, 267: 17748-17752). Residues of the hydrophobic strip □ positions were generally sensitive; the C-terminal strip residues were particularly sensitive. The sensitivities to substitutions of groups of residues in T4 lysozyme, including those occupying the structural positions described above, are compared in Table XIV. The protein as a whole scored 16; that is, 16% (328/2015) of substitutions tested were found to be deleterious. Buried residues, as a group, were more sensitive to substitutions. Loss of function resulted from 38% of substitutions for residues with side chains which have less than 12% of their surface areas accessible to solvent; this sensitivity increased to 42% if the group was restricted to those residues with completely inaccessible side chains. These observations establish a criterion for the performance of a scheme to pick out critical residues.

This example demonstrates the minimal structural change to destroy function of a molecule by altering a residue in the longitudinal hydrophobic strip, most specificially at the C-terminus, from a leucine, isoleucine, valine, phenylalanine, or methionine to another residue not in that group. The altered molecule would have a primary sequence close to the wild type but no biological activity. Such changes may be applied to vaccine development against toxins from various sources as isolated proteins or in the context of site-specific mutation of a pathogen to destroy a virulence factor in an otherwise infectable particle. This is a new approach to the rational design of attenuated pathogens for vaccination purposes.

TABLE XIV

Sensitivities of positions in T4 lysozyme to amino acid substitutions

| Group | No. of residues | Substitutions (n) | Score | Residues represented | Expected score | Difference | P |
|---|---|---|---|---|---|---|---|
| All residues | 163 | 2015 | 16 | all | (16) | 0 | — |
| >88% Buried | 50 | 621 | 38 | ACDFGILMNRSTVWY | 20 | 18 | <.001 |
| 100% Buried | 24 | 302 | 42 | ACDFGILMNTVY | 19 | 23 | <.001 |
| Conserved | 14 | 172 | 47 | ADEGHLTWY | 22 | 25 | <.001 |

TABLE XIV-continued

Sensitivities of positions in T4 lysozyme to amino acid substitutions

| Group | No. of residues | Substitutions (n) | Residues Score represented | | Expected score | Difference | P |
|---|---|---|---|---|---|---|---|
| α-Helical | 97 | 1200 | 16 | all but H | 15 | 1 | — |
| Hydrophobic strip | 25 | 307 | 26 | ACFIKLVW | 19 | 7 | <.001 |
| N-terminal | 9 | 110 | 26 | AIKLW | 18 | 8 | <.05 |
| C-terminal | 9 | 111 | 44 | FLIVW | 24 | 20 | <.0001 |
| Smallest | 9 | 111 | 31 | AILVW | 18 | 13 | <.001 |
| N-Shoulders | 3 | 36 | 14 | KL | 16 | −2 | — |
| C-Shoulders | 7 | 86 | 31 | CFIL | 20 | 11 | <.01 |
| Virtual N-terminal | 8 | 97 | 10 | FGKLRST | 15 | −5 | — |
| Virtual C-terminal | 9 | 112 | 31 | EGILNRST | 18 | 13 | <.001 |
| Non-strip | 72 | 880 | 13 | all but C & H | 15 | −2 | <.05 |

EXAMPLE 11

Discovery of Favored and Suppressed Patterns of Hydrophobic and Nonhydrophobic Amino Acids in Protein Sequences Ultraearly events in protein folding may be influenced by short sequence motifs which collapse with the least ambiguity into the molten globule nucleations which initiate secondary structure (Kauzmann, W. (1959) *Adv. Prot. Chem.*, 14, 1–63; Dill, K. A. (1989) *Biochemistry*, 24, 1501–1509; Kuwajima, K. (1989) *Proteins*, 6, 87–103; Dill, K. A., et al., (1993) *Proc. Natl. Acad. Sci. USA*, 90, 1942–1946). Since hydrophobic residues Leu, Ile, Val, Phe, and Met (LIVFM) are the largest subset of residues with chemically similar side chains (combined frequency 0.2525 in the proteins studied), they dominant such local motifs, as reflected in their distribution as not-too-many and not-too-few together. Too many adjacent hydrophobic amino acids in a short segment may lead to many folding pathways of comparable energy levels, leading to multiple, malfunctional final forms, and thus be selected against on an evolutionary basis. In contrast, too few hydrophobic residues without other strong, structure-determining motifs may lack the initial restriction on forms afforded by selective placement of hydrophobic residues and consequently also lead to multiple, final forms. An optimal frequency of hydrophobic (or conversely nonhydrophobic) runs would be created by these competing tendencies. To test this hypothesis that hydrophobic residues might not be distributed in a random fashion, certain 5-residue patterns were examined for preferential or suppressed occurance. A correlation between preferred patterns and associated secondary structures was then identified in mature proteins. The frequencies of runs of hydrophobic LIVFM residues and of nonLIVFM residues were determined in 48 proteins (8024 amino acids) (Table XV). Those frequencies were compared to the expected frequencies for the random placement of such residues in proteins. While the frequencies of single or two adjacent hydrophobic residues approximated the respective random expectations, the observed frequency of runs of three or more hydrophobic residues were less than expected (p<0.01). The frequency of runs of nonhydrophobic residues was not suppressed to a similar degree in shorter runs; only at the level of 6 nonhydrophobic residues did z=−2.1 (corresponding to p<0.05).

The counts of the number of occurrences of a template within a protein (or of a pattern within a template) were treated as binomial random variables with N possible positions and the proportion, P, equal to the empirical frequency of the pattern over all proteins under study. An empirical distribution is that subset of random distributions of residues when the frequency of each type of residue in the distribution is equal to the frequency in the overall population. When the term random distribution is used by others, they usually mean empirical distribution. The observed counts, X, had mean, NP, and variance, NP(1−P). The observed proportion, X/N, had variance, P(1−P)/N. With a value of $P_o$ under the null hypothesis, the z score was then $(X/N-P_o)/\sqrt{P(1-P)/N}$ where z was approximately normally distributed. To avoid misinterpretations arising from multiple testings (type I statistical errors), statistical significance was restricted to one-tailed probabilities (p-values) of p<0.01 for |z|=2.6 and p<0.001 for |z|=3.3.

Analyses were completed with 48 proteins with known crystallographic structure and the following Brookhaven file codes: 1BP2, 1CPV, 1CRN, 1CRO, 1ECA, 1EDC, 1EMQ, 1GP1, 1INS,C, 1INS,D, 1LZ1, 1MBO, 1PPT, 1RHD, 1SBT, 1SN3, 2ACT, 2APP, 2AZA, 2BSC, 2CAB, 2CYP, 2CCY, 2CDV, 2LHB, 2LZM, 2MBN, 2MLT, 2OVO, 2PAB, 2SNS, 2SSI, 2STV, 3ADK, 3C2C, 3CYT, 3GRS, 3TLN, 351C, 4DFR, 4FXN, 4LDH, 5CPA, 5RSA, 5PTI, 6ADH, 7CAT, 7LYZ.

TABLE XV

Divergence between observed and expected frequencies of run of hydrophobic and nonhydrophobic residues

| | Hydrophobic | | | | Nonhydrophobic | | | |
|---|---|---|---|---|---|---|---|---|
| | Nested | | Exclusive | | Nested | | Exclusive | |
| Runs | Observed | z score | Observed | z score | Observed | z score | Observed | z score |
| 1 | 2046 | 0.0 | 1098 | −0.8 | 5998 | 0.0 | 337 | −2.0 |
| 2 | 513 | 0.2 | 335 | 3.4 | 4464 | 0.2 | 333 | 3.3 |
| 3 | 98 | −2.6 | 64 | −0.6 | 3267 | −1.0 | 224 | 1.1 |
| 4 | 18 | −2.5 | 14 | −0.8 | 2403 | −1.4 | 163 | 0.6 |
| 5 | 2 | −2.1 | 2 | −1.1 | 1763 | −1.7 | 128 | 1.2 |
| 6 | 0 | −1.4 | 0 | −1.0 | 1286 | −2.1 | 89 | 0.3 |
| 7 | | | | | 937 | −2.4 | 80 | 2.0 |
| 8 | | | | | 677 | −2.8 | 48 | 0.0 |
| 9 | | | | | 497 | −2.6 | 40 | 0.7 |
| 10 | | | | | 365 | −2.5 | 29 | 0.5 |
| 11 | | | | | 273 | −2.0 | 18 | −0.4 |
| 12* | | | | | 210 | −1.2 | 10 | −1.2 |

*All subsequent runs had a frequency of ≦ 8.

EXAMPLE 12

Favored and Suppressed Patterns of Hydrophobic Residues

Five-position templates (with all combinations of LIVFM and nonLIVFM residues) were scored across the 48 proteins (Table XVI). Z scores are presented for the patterns arranged in a binomial progression (Table XVIA) or to emphasize dependence on spacing (Table XVIB). Z scores for selected combinations of favored motifs and contrasting patterns, are presented in Table XVII. Certain combinations of ◊♦♦◊◊ and ♦◊◊♦◊ patterns are significantly preferred.

TABLE XVIA

Patterns of LIVFM ♦ and nonLIVFM ◊ residues and z scores for differences between frequencies which were observed versus expected under an hypothesis for an empirical distribution of residues

| | | | | | |
|---|---|---|---|---|---|
| ◊◊◊◊◊ | 1.7* | ◊♦◊♦♦ | −0.1 | ♦◊♦♦◊ | 2.2 |
| ◊◊◊◊♦ | −0.1 | ◊♦♦◊◊ | 3.5 | ♦◊♦♦♦ | −1.6 |
| ◊◊◊♦♦ | −0.4 | ◊♦♦◊♦ | 0.3 | ♦♦◊◊◊ | 1.6 |
| ◊◊◊♦♦ | 0.8 | ◊♦♦♦◊ | −0.8 | ♦♦◊◊♦ | 2.5 |
| ◊◊♦◊◊ | 2.1 | ◊♦♦♦♦ | −1.6 | ♦♦◊♦◊ | −1.6 |
| ◊◊♦◊♦ | 1.7 | ♦◊◊◊◊ | 0.2 | ♦♦◊♦♦ | 1.9 |
| ◊◊♦♦◊ | 2.1 | ♦◊◊◊♦ | 0.5 | ♦♦♦◊◊ | −1.0 |
| ◊◊♦♦♦ | −0.8 | ♦◊◊♦◊ | 2.4 | ♦♦♦◊♦ | −1.2 |
| ◊♦◊◊◊ | −0.6 | ♦◊◊♦♦ | 1.4 | ♦♦♦♦◊ | −1.6 |
| ◊♦◊◊♦ | 1.9 | ♦◊♦◊◊ | −2.7 | ♦♦♦♦♦ | −2.1 |
| ◊♦◊♦◊ | −3.4 | ♦◊♦◊♦ | −3.1 | | |

*At a p<0.01, one would expect to find 0.3 of the 32 patterns with an absolute value of z > 2.6.

TABLE XVIB

Patterns of LIVFM (♦) and nonLIVFM (◊) residues, with z scores, arranged to emphasize dependence on spacing

| | |
|---|---|
| ♦♦◊◊◊ | 1.6 |
| ♦◊♦◊◊ | −2.7 |
| ♦◊◊♦◊ | 2.4 |
| ♦◊◊◊♦ | 0.5 |
| ♦♦◊◊◊ | 1.6 |
| ◊♦♦◊◊ | 3.5 |
| ◊◊♦♦◊ | 2.1 |
| ◊◊◊♦♦ | 0.8 |
| ♦◊♦◊♦ | −3.1 |
| ◊♦◊♦◊ | −3.4 |

TABLE XVII

Patterns of LIVFM (♦) and nonLIVFM (◊) residues arranged to emphasize combinations of some favored and suppressed patterns of Table XVIA.

| | |
|---|---|
| ◊♦♦◊ | 3.2 |
| ◊◊♦♦◊ | 2.1 |
| ◊♦♦◊◊ | 3.5 |
| ◊◊♦♦◊◊ | 2.1 |
| ♦◊◊♦♦◊◊ | 3.1 |
| ◊◊♦♦◊◊♦ | 3.4 |
| ♦◊♦♦◊◊♦ | 3.0 |
| ◊♦◊◊♦♦◊♦ | 3.6 |
| ♦◊♦♦◊◊♦◊ | 3.2 |
| ◊◊♦♦◊◊♦◊ | 4.7 |
| ◊◊♦♦◊◊♦◊◊ | 5.1 |
| ◊♦♦◊◊♦◊◊♦ | 4.7 |
| ◊♦♦◊◊♦◊◊♦◊ | 4.1 |
| ◊◊♦♦◊◊♦◊◊♦◊ | 5.0 |
| ♦◊♦◊◊♦♦◊◊♦◊ | 3.7 |
| ◊◊♦◊◊♦♦◊◊♦◊ | 4.5 |
| ◊◊◊♦◊◊♦♦◊◊♦◊ | 3.5 |
| ◊◊◊◊♦◊◊♦♦◊◊♦◊ | 3.9 |
| ◊◊◊◊♦◊◊♦♦◊◊♦◊◊ | 3.4 |
| ♦♦◊♦◊♦◊♦◊ | −2.5 |
| ◊♦◊◊♦◊ | 1.1 |
| ◊♦◊◊♦◊◊♦◊ | 0.8 |
| ◊♦◊♦◊♦◊ | −0.5 |
| ◊♦♦◊◊♦♦◊ | 0.4 |
| ◊♦♦◊♦♦◊◊♦♦◊ | −0.6 |

EXAMPLE 13

Distributions of Nonhydrophobic Residues within Preferred Motifs

The distributions of all non Leu, Ile, Val, Phe, Met (nonLIVFM) residues in each ◊ position of the templates were counted and z scores were calculated for the differences between observed frequencies and the frequencies of those residues in positions not occupied by LIVFM. Scores for |z|>1.96 (p<0.05) are given. Table XVIII reports distributions of amino acids around two sequential hydrophobic residues. The nonLIVFM position immediately preceding two hydrophobic residues showed an increased frequency of Arg and decreased frequencies of Asn and Tyr. The frequency of Glu was increased in the nonLIVFM position 2 residues before the first hydrophobic position. A polarity was seen in distributions of nonhydrophobic residues about the two hydrophobic residues: negatively charged residues were favored before but not after the pair of hydrophobic amino acids. Such patterns of preferred pairings of amino acids among positions of oligopeptide sequences has been observed by others (Cserzö, M. et al., (1989) *Int. J. Peptide Protein Res.*, 34, 184–195; Klapper, M. H. (1977) *Biochem. & Biophys. Res. Comm.*, 78, 1018–1024).

Table XIX shows the distributions of nonLIVFM residues about a single hydrophobic residue. Cys was suppressed in the position before the single LIVFM. Glu was increased in the second position preceding the hydrophobic residue, and Gly, Pro, and Tyr were suppressed in that position. Gly was suppressed in the position after the single hydrophobic residue and Lys was favored in the first position following the single hydrophobic residue. Table XX presents patterns with single ♦ or double ♦♦ hydrophobic residues when such combinations were favored in the hydrophobic templates of Table XVI. In general, the patterns of amino acids in ◊ positions of these combinations were what would be expected from combination of individual patterns.

TABLE XVIII

Distributions of nonLIVFM residues in ◊ positions around ♦♦ positions in certain templates

| | | | ◊ | ♦ | ♦ | ◊ | |
|---|---|---|---|---|---|---|---|
| | | N | −2.1 | | | | |
| | | R | 3.1 | | | | |
| | | Y | −2.6 | | | | |
| | | —[a] | 2.8 | | | | |
| | ◊ | | ◊ | ♦ | ♦ | ◊ | |
| E | 3.1 | N | −2.2 | | | | |
| | | R | 2.6 | | | | |
| | | Y | −2.3 | | | | |
| | | | ◊ | ♦ | ♦ | ◊ | ◊ |
| | | K | 3.0 | | | | |
| | | N | −2.2 | | | | |
| | | P | −2.1 | | | P −2.2 | |
| | | R | 2.2 | | | | |
| | | Y | −2.2 | | | | |
| | | — | 3.4 | | | | |
| | ◊ | | ◊ | ♦ | ♦ | ◊ | ◊ |
| | | N | −2.0 | | | | |
| | | P | −2.1 | | | | |
| — | 2.1 | | | | | | |

[a] — = D or E

TABLE XIX

Distributions of nonLIVFM residues in ◊ positions around ✦ positions in certain templates

| ◊ | ✦ | ◊ |
|---|---|---|
| C −2.3 | | |

| ◊ | ◊ | ✦ | ◊ |
|---|---|---|---|
| | C −2.4 | | |
| E 2.1 | | | |
| G −2.2 | | G −2.1 | |
| P −2.2 | | | |
| —ᵃ 2.3 | | | |

| ◊ | ◊ | ✦ | ◊ | ◊ |
|---|---|---|---|---|
| | C −2.4 | | | E −2.4 |
| A 2.3 | | | | |
| | C −2.4 | | | |
| E 2.5 | | | | E −3.0 |
| G −2.1 | | | G −2.7 | |
| | | | K 2.0 | |
| P −2.6 | | | | |
| | | | | W 2.0 |
| Y −2.1 | | | | |
| | | | | —2.4 |

ᵃ— = D or E

TABLE XX

Distributions of nonLIVFM residues in ◊ positions around ✦✦ and ✦ positions in certain templates

| ◊ | ◊ | ✦ | ✦ | ◊ | ◊ | ✦ | |
|---|---|---|---|---|---|---|---|
| D 3.0 | | | | | | | |
| E 2.4 | | | | | | | |
| | | T 2.4 | | | | | |
| —ᵃ 4.0 | | | | | | | |

| ◊ | ◊ | ✦ | ✦ | ◊ | ◊ | ✦ | ◊ |
|---|---|---|---|---|---|---|---|
| D 2.9 | | | | | | | |
| E 2.2 | | | | | | | |
| — 3.8 | | | | | | | |
| | | T 2.3 | | | | | |
| | | | | | | | K 2.7 |
| | | | | | Y 2.1 | | |
| ✦ ◊ | ◊ | ✦ | ✦ | ◊ ◊ | | ✦ | ◊ |
| | | | | E 2.0 | | | |
| | | | | G −2.7 | | | |
| | | | | — 2.7 | | | |
| | K −2.0 | | | | | | |
| | R 2.6 | | | | | | |

—ᵃ = D or E

EXAMPLE 14

Distributions of φ and ψ at Each Position of the Preferred Pattern ◊ ✦ ✦ ◊ ◊

In order to test whether a favored pattern of hydrophobic and nonhydrophobic residues associates with secondary structures, Ramachandran plots were made for φ versus ψ angles at residues in each position of sequences fitting the ◊ ✦ ✦ ◊ ◊ pattern. Percentages of residues with φ and ψ angles falling within α-helix and β-sheet regions of Ramachandran plots for positions 1 through 5 of the template ◊ ✦ ✦ ◊ ◊ are presented in Table XXI. For the subset of sequences with φ, ψ angles at position 2 within limits for α-helices, the percentages at each template position of residues with φ, ψ angles within limits for α-helices were: 1–89%, 2–100%, 3–87%, 4–76%, 5–66%. Comparably, for the subset of sequences with φ, ψ angles at position 2 within limits for β-strands, the percentages at each template position of residues with φ, ψ angles within limits for β-strand were: 1–70%, 2–100%, 3–83%, 4–78%, 5–43%. That is, residues around position 2 usually demonstrated the same α-helical or β-strand conformation found at position 2.

TABLE XXI

Percentage of residues at each position in the pattern ◊ ✦ ✦ ◊ ◊ with $C_\alpha$, φ, ψ values within the indicated limits

|  | α-helix | β-sheet |
|---|---|---|
| φ limits | −65, −15 | +90, +180 |
| ψ limits | −45, −100 | −45, −165 |
| Position: | | |
| 1 | 57 | 26 |
| 2 | 57 | 29 |
| 3 | 55 | 34 |
| 4 | 48 | 31 |
| 5 | 46 | 23 |

EXAMPLE 15

Association of the ◊ ✦ ✦ ◊ ◊ Motif with α-Helical or β-Strand Configurations

The favored pattern ◊ ✦ ✦ ◊ ◊ occurs in sequences which have α-helical, β-strand, or other conformations (Table XXII). However, the association of that pattern is greater when the second position of the sequence has φ, ψ angles within α-helical limits (z=+3.6), than when the second position of the sequence has β-strand conformation (z=−1.0). Recalculation of an expected frequency of LIVFM in the ◊ ✦ ✦ ◊ ◊ to weight at 0.4 (the frequency of LIVFM amino acids in the pattern) the fraction of residues with φ, ψ angles of α-helices, did not alter the significance of the association of ◊ ✦ ✦ ◊ ◊ with sequences with α-helical φ, ψ angles at position 2.

The distributions of nonLIVFM amino acids was determined in ◊ positions sequences fitting the ◊ ✦ ✦ ◊ ◊ patterns, when the second position had φ, ψ angles of either α-helices or β-strands. In the 94 sequences with second positions having α-helical φ, ψ angles, the only associations at p<0.01 were position 1: Arg, z=3.4; position 5: Gly, z=−2.1. In the 46 sequences with second positions having β-strand φ, ψ angles, the only associations at p<0.01 were position 1: Arg, z=2.5, and Trp, z=2.2; position 3: Gly, z=−1.9, Thr, z=2.4, and Tyr, z=1.8. There was no pattern obviously distinguishing α-helical from β-strand sequences fitting the ◊ ✦ ✦ ◊ ◊ template.

TABLE XXII

Frequencies of φ, ψ angles within limits of α-helices or β-strands for all, ✦ or ◊ residues and second positions ◊ ✦ ✦ ◊ ◊

|  | all | ✦ | ◊ | pattern | nᵃ | zᵇ |
|---|---|---|---|---|---|---|
| α-helix | .41 | .45 | .39 | 0.58 | 94 | +3.6 |
| β-strand | .33 | .40 | .31 | 0.28 | 46 | −1.0 |
| other | .26 | .15 | .30 | 0.14 | 31 | −0.5 |
| total | 1.00 | 1.00 | 1.00 | 1.00 | 161 | |

ᵃnumber of patterns with second position φ, ψ angles within indicated limits
ᵇz score of pattern frequencies compared to frequencies over all positions

EXAMPLE 16

Distributions of LL in ☐ Positions of Hydrophobic Strips-of-Helix

The occurrence of two sequential amino acids from the group Leu, Ile, Val, Phe, Met with one residue in a ☐ position was termed LL. The frequency of such LL events in N-terminal, C-terminal, and middle (between N- and C-terminal positions) ☐ positions in the longitudinal stripof-helix were determined (Table XXIII). LL occurred more often in middle □ positions of the helix and were suppressed at the N-terminus. Skewing of LL □ toward one end or the other of the strip was determined in terms of the relative distance of each LL □ as a fraction of the number of □ positions along the helix from the N-terminus. For example, a LL in □ position 4 of a strip with five □ positions, occurred at 0.75. The mean distribution of LL was 0.60. The mean distribution of LL was not significantly removed from the middle of the strip.

TABLE XXIII

Distributions of LL in □ positions of helical hydrophobic strips.

| | Distribution* | | |
|---|---|---|---|
| | □ positions total | □ positions with LL | Z score |
| N-termini | 211 | 22 | −4.6 |
| middle | 371 | 112 | 3.7 |
| C-termini | 211 | 52 | 0.4 |
| total | 793 | 186 | |

*In this analysis 48 proteins, containing 8024 residues, 2827 of which were in helices were scored for LL. LL were more frequently found in helices than expected for an empirical distribution over the entire protein sequence (z score = 3.5).

EXAMPLE 17

Distributions of Hydrophobic Amino Acids at N- and C-termini of Alpha Helices

Most residues in ○ positions between the terminal □ position in the longitudinal, hydrophobic strip and the first virtual □ position tend to fold as part of the α-helix. The actual frequency of the distribution of intervening ○ positions in 227 helices and their adjacent sequences in 48 proteins was compared to the hypothesis that the helices would terminate with equal frequencies in the terminal strip □ and intervening ○ positions (Table XXIV). The preference for intervening ○ positions to fold in the α-helices was reflected in cumulative z-scores: N-termini 1.8, C-termini 3.8, both termini 4.0 (p<0.001).

TABLE XXIV

Distributions of amino acids at N- and C-termini of α-helices showing that helices tend to start and terminate with the ○ position nearest the first virtual □ position beyond the N- and C-termini, respectively

| | Prediction | Observed | Expected | z score |
|---|---|---|---|---|
| N-terminus | +++□[1] | 56 | 38 | +3.2 |
| | −++□ | 34 | 38 | — |
| | −−+□ | 38 | 38 | — |
| | −−−□ | 30 | 38 | — |
| C-terminus | □+++ | 62 | 38 | +4.3 |
| | □++− | 13 | 38 | −4.4 |
| | □+−− | 41 | 38 | — |
| | □−−− | 22 | 38 | −2.8 |
| | □++ | 27 | 25 | — |
| | □+− | 25 | 25 | — |
| | □−− | 38 | 25 | +2.9 |

[1]□ = terminal □ position, with the residue in this position always being in the helix by definition.
+ = distal ○ position before the first virtual ○ position, with the residue in this ○ position being in the helix.
− = distal ○ position before the first virtual ○ position, with the residue in this ○ position not being in the helix.

EXAMPLE 18

Demonstration of Strucutral Effects of Design Characteristic Specified by the Method of the Invention Materials and Methods Peptide synthesis and analysis. PH-1.0 (FIG. 1) was synthesized by the Merrifield solid state synthesis method with t-BOC reagents. It was dissolved in 0.1% trifluoroacetic acid in water, desalted by adsorption to Sep-Pak C18 cartridges, and eluted with 30% acetonitrile in 0.1% trifluoroacetic acid. The peptide was purified by reverse phase HPLC on a C18 column with an acetonitrile gradient in 0.1% trifluoroacetic acid. Peptide composition was verified by amino acid analysis and confirmed by 1D $^1$H NMR spectroscopy.

Sample preparation. NMR samples were prepared by dissolving peptides in 700 μl of 90% $H_2O$/10% $D_2O$ or 50% trifluoroethanol-$d_2$/$H_2O$ to a final concentration of 1–5 mM. The pH of the solutions was adjusted with 0.01M NaOH or HCl directly in the NMR tube and measured with a glass electrode without correcting for isotope effects. Micelle solutions were prepared by dissolving 180 mg of SDS-$d_{25}$ (Cambridge Isotopes, Woburn, Mass.) in 500 μl of 90% $H_2O$/10% $D_2O$, and sonicating to assure dissolution. 200 μl of a concentrated peptide solution in 90% $H_2O$/10% $D_2O$ were added to the micelles yielding about 6.5 mM peptide, and the pH was adjusted. The concentration of SDS-$d_{25}$ was well above the micelle critical concentration with an estimated peptide:micelle ratio of 1:1.4, thus minimizing the concentration of unbound peptide without sacrificing the sensitivity of the NMR signals. Sodium 3-(trimethylsilyl) propionate-2,2,3,3-$d_4$ was used as the internal reference in all cases.

NMR experiments. Proton NMR spectra were acquired on a Varian UNITY series 500 MHz spectrometer with the use of the $^1$H channel of a triple resonance probe ($^1$H/$^{13}$C/$^{15}$N) (Varian Analytical Instruments, Palo Alto, Calif.). Spectra were processed using VnmrS v4.1 and VnmrX software on SUN 4–65 and 4–60 computers.

1D $^1$H spectra were acquired at 5° C. intervals from −5° C. to 55° C. Water suppression was accomplished by continuous wave, low power irradiation of the water resonance through the transmitter channel during 1 sec prior to the 90° pulse, a feature incorporated in all the pulse sequences. A polynomial baseline correction and an exponential line broadening were used in the processing of these spectra. The center of transmitter frequency was set at the water resonance for all experiments.

2D NMR experiments were acquired in the phase sensitive mode using the States-Haberkorn hypercomplex method. Water suppression was accomplished as above where the presaturation period (0.5 sec) was incorporated into the 2D pulse sequence through the transmitter. 2D spectra were apodized using a gaussian window function in the t2 and t1 dimensions.

2D $^1$H TOCSY experiments were acquired with 2048 data points in the t2 dimension and 2×256 t1 increments, with 32 scans per t1 value, a pulse delay of 0.1 sec and a MLEV16 mixing period of 80 or 120 ms. The final 2D spectra were processed with zero-filling to a final spectrum size of 2048×2048 data points.

2D $^1$H NOESY experiments were acquired with 4096 data points in the t2 dimension and 2×512 t1 increments, with 64 scans per t1 value, a pulse delay of 0.1 sec, and a mixing time of 200 ms. The final 2D spectra were processed with zero-filling to a final spectrum size of 4096×4096 data points. With the use of NOE buildup rates, which were determined by varying the mixing times from 40–300 ms, it was determined that spin diffusion effects did not occur at mixing times below 250 ms.

3D structure. Interproton distance constraints were derived from the NOESY spectra. NOESY crosspeaks were assigned and classified according to their intensities as strong, medium and weak with the use of their volume integrals. Distances associated with these ranges were calibrated using the intensity of the crosspeak corresponding to known fixed interproton distances, i.e. the ortho and meta aromatic protons of Tyr (2.5 Å). The following constraint ranges were used: 1.8–2.7 Å for strong, 1.8–3.5 Å for medium and 1.8–5.0 Å for weak crosspeaks, respectively. The bounds of the constraint distances were modified for methyl groups, degenerate aromatic ring resonances, and methylene protons without stereospecific assignments, according to the pseudo-atom approach.

RESULTS

Testing the Stabilizing Function of Two Sequential LIVFM Residues Crossing the Longitudinal Hydrophobic Strip-of-Helix Analysis of amino acid distributions about α-helices, which are compared after justification on their longitudinal, hydrophobic strips-of-helix, leads to the recognition of highly restricted placements of certain amino acids in and about α-helices. Those placements appear to reflect the roles of those amino acids in helix formation and stability. The longitudinal hydrophobic strip-of-helix is found by application of a template (□●▲●□○○□●▲●□○○□●▲○, joined in a circle) to the primary sequence of an α-helix in a protein to maximize the mean hydrophobicity of residues in □ positions. The frequency of LL (occupancy of an □ position with an amino acid of the group LIVFM when the preceding or the following position in the primary sequence was also from the group LIVFM) was determined in N-terminal, C-terminal, and middle (between N- and C-terminal) □ positions in the longitudinal strip-of-helix for 48 proteins. LL occurred more often in middle □ positions of the helix and were suppressed at the N-terminus. Skewing of LL toward one end or the other of the hydrophobic strip was tested in terms of the relative distance of each LL □ as a fraction of the number of □ positions along the helix from the N-terminus. For example, a LL in the fourth □ position of a strip with five □ positions, occurred at 0.75. The mean distribution of LL was 0.60 and was not significantly removed from the middle of the strip.

In order to demonstrate that the presence of LL at a □ position between the distal N- and C-terminal □ positions in the longitudinal hydrophobic strip led to greater stability of a peptidyl sequence, the conformations and stability of PH-1.0 was compared with that of PH-1,12 which had a LL at the third □ position resulting from a Thr$^9$→Leu substitution. Relative to PH-1.0, PH-1.12 (FIG. 1) demonstrated increased chemical shifts at C$^\alpha$ of Gln$^6$, Gln$^{10}$, and Lys$^{13}$ which lay in the helical loops adjacent to the LL structure. There was also an increase in the chemical shift at the C$^\alpha$ of Leu$^8$, but no alteration was seen in the chemical shifts at the C$^\alpha$H of Leu$^5$, Leu$^9$, and Leu$^{12}$. In contrast, in 50% TFE/H$_2$O the chemical shifts at each residue position in all three peptides were comparable, indicating the specificity of the variations seen in the SDS micelle-adsorbed conformations.

Testing the Hypothesis that Favored and Disfavored Motifs of LIVFM Residues Correlate to Degree of Order in Micelle-Adsorbed Peptides Hydrophobic amino acids of the group LIVFM are distributed in favored or suppressed patterns within protein sequences. The frequencies of all 5-position combinations of ◆=LIVFM and ◇=nonLIVFM residues were analyzed in 48 proteins of known crystallographic structure. Some motifs were strongly preferred or dispreferred, e.g. ◇◆◆◇◇ was favored (z=3.5), while ◇◆◇◆◇ was not (z=−3.4). In longer patterns, ◆◆ followed by ◇◇ and one ◆ was favored (◇◇◆◆◇◇◆◇◇, z=5.1), while conversion of the single hydrophobic residue to a pair was not (◇◇◆◆◇◇◆◆◇, z=0.8). While the strongly favored pattern ◇◆◆◇◇ was found in both α-helical and β-strand sequences, it associated significantly with α-helices (z=3.6 for the second position φ, ψ angles of α-helices), but was also not significantly suppressed in β-strands (z=−1.1). Such selections for certain motifs of LIVFM and non LIVFM residues might occur if they lead efficiently to the local nucleations hypothesized to characterize molten globule intermediates in the folding of proteins, regardless of the final local secondary structure in which those motifs appear.

In order to demonstrate that favored or disfavored motifs of Leu, Ile, Val, Phe, and Met residues leads to greater or lesser stability, respectively, of adsorbed amphiphilic α-helices, the conformations and stability of PH-1.0 was compared with that of PH-1.13 (with substitution of Gln$^{10}$→Leu). The patterns of these peptides were: PH-1.0 ◆◇◇◇◆◇◇◆◇◇◇⇓◇ and PH-1.13 ◆◇◇◇◆◇◇◆◇◆◇◆◇. The homolog LYQELQKLTLTLK (SEQ ID NO: 3) (with a disfavored pattern of three alternating Leu residues, z=−3.4) demonstrated decreased chemical shift at the C$^\alpha$H of each residue from Gln$^6$ to Lys$^{13}$. The chemical shifts of C$^\alpha$H of residues from Leu$^1$ through Leu$^5$ were comparable.

In addition to demonstrating destabilization of local structure in the comparison of PH-1.13 relative to PH-1.0, increased stabilization of PH-1.12 (◆◇◇◇◆◇◇◆◆◇◇◆◇) was found relative to PH-1.0 by introduction of the favored ◇◇◆◆◇◇◆◇◇, z=5.1. The LL-hydrophobic strip and 'binary motif' correlations with local stability reflect a basic geometric mechanism regulating stabilization of peptidyl sequences folding against hydrophobic regions, for example, in the initial phase of protein folding or in the binding of a hormone to its receptor.

Figure 1B:
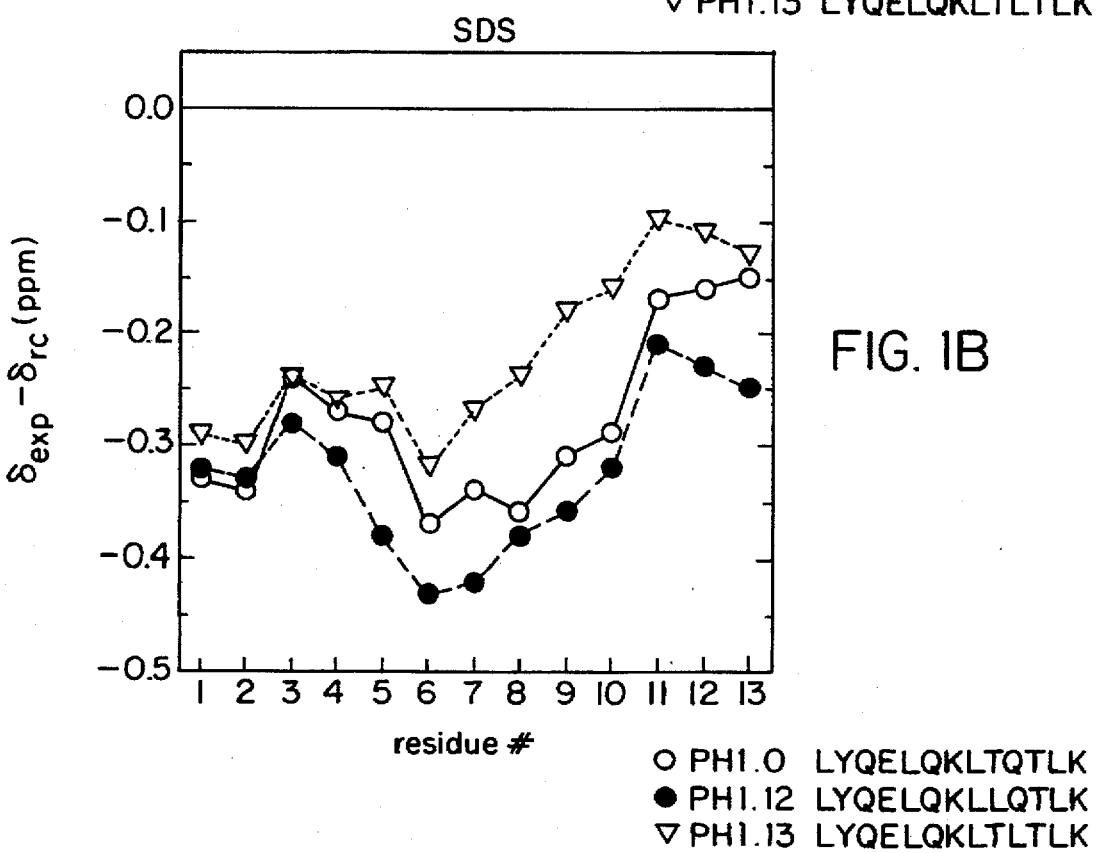

In FIG. 1, the difference between the experimentally observed (exp) and random coil (rc) values of the chemical shifts for the C$^\alpha$H at each residue position in three peptides is plotted from NMR analyses in 50% trifluorethanol/water (TFE) and on sodium dodecylsulfate micelles (SDS). The value presented at each residue position, n, is the mean of values observed at n−1, n, and n+1. The chemical shifts reflect the degree of order in structure about the C$^\alpha$ in these peptides for which alpha helical conformation was demonstrated by various cross correlations. While the three peptides had comparable degrees of order about each C$^\alpha$H in TFE, order on SDS micelles about each C$^\alpha$H followed predictions precisely. Increased helical stability was demonstrated in helical loops surrounding the LL structure and decreased order was found in the region of the ◆◇◆◇◆ structure.

EQUIVALENTS

Those skilled in the art will recognize, or be able to ascertain using no more than routine experimentation, many equivalents to the embodiments of the invention described specifically herein. Such equivalents are intended to be encompassed in the scope of the following claims.

I claim:

1. A method for designing an amino acid copolymer in which two helices will cross, comprising:

a) providing the primary amino acid sequence of the amino acid copolymer including the known or putative helices;

b) applying a longitudinal strip-of-helix template comprising the residue classes:

□●▲●□○○□●▲●□○○□○▲○ to the determined amino acid sequence of the known or putative helix to maximize the mean hydrophobicity of residues in □ positions;

c) comparing the template-predicted residues with the actual residues;

d) altering residues of the amino acid copolymer at the □ positions at which the helices are to cross to alanine or valine, thereby enhancing the probability for crossing at that position.

* * * * *